US010912754B2

(12) United States Patent
Carter et al.

(10) Patent No.: US 10,912,754 B2
(45) Date of Patent: *Feb. 9, 2021

(54) METHODS AND COMPOSITIONS FOR TREATING EXCESSIVE SLEEPINESS

(71) Applicant: Jazz Pharmaceuticals Ireland Limited, Dublin (IE)

(72) Inventors: Lawrence Patrick Carter, Palo Alto, CA (US); Yuan Lu; Katayoun Zomorodi, San Jose, CA (US)

(73) Assignee: Jazz Pharmaceuticals Ireland Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 16/877,717

(22) Filed: May 19, 2020

(65) Prior Publication Data

US 2020/0281886 A1    Sep. 10, 2020

Related U.S. Application Data

(63) Continuation of application No. 16/618,735, filed as application No. PCT/US2018/035532 on Jun. 1, 2018.

(60) Provisional application No. 62/514,176, filed on Jun. 2, 2017.

(51) Int. Cl.
```
A61K 31/27      (2006.01)
A61K 9/00       (2006.01)
A61K 9/20       (2006.01)
A61K 9/48       (2006.01)
A61P 25/00      (2006.01)
```

(52) U.S. Cl.
CPC ............ *A61K 31/27* (2013.01); *A61K 9/20* (2013.01); *A61K 9/48* (2013.01); *A61P 25/00* (2018.01); *A61K 9/0053* (2013.01)

(58) Field of Classification Search
CPC ........ A61K 31/27; A61K 9/0053; A61K 9/20; A61K 9/48; A61P 25/00
See application file for complete search history.

(56) References Cited

U.S. PATENT DOCUMENTS

| | | | |
|---|---|---|---|
| 4,335,138 A | 6/1982 | Wiersdorff et al. | |
| 5,705,640 A | 1/1998 | Choi et al. | |
| 5,756,817 A | 5/1998 | Choi et al. | |
| 5,955,499 A | 9/1999 | Choi et al. | |
| 6,140,532 A | 10/2000 | Choi et al. | |
| 6,562,867 B2 | 5/2003 | Plata-Salaman et al. | |
| 6,589,985 B2 | 7/2003 | Plata-Salaman et al. | |
| 6,680,299 B2 | 1/2004 | Or et al. | |
| 6,680,322 B2 | 1/2004 | Castelhano et al. | |
| 6,680,324 B2 | 1/2004 | Castelhano et al. | |
| 7,078,436 B2 | 7/2006 | Plata-Salaman et al. | |
| 8,232,315 B2 | 7/2012 | Lee et al. | |
| 8,440,715 B2 | 5/2013 | Ahnaou et al. | |
| 8,552,060 B2 | 10/2013 | Palumbo et al. | |
| 8,623,913 B2 | 1/2014 | Melnick et al. | |
| 8,729,120 B2 | 5/2014 | Sporn | |
| 8,741,950 B2 | 6/2014 | Khayrallah et al. | |
| 8,778,398 B2 | 7/2014 | Rourke et al. | |
| 8,895,609 B2 | 11/2014 | Lee et al. | |
| 8,927,602 B2 | 1/2015 | Lee et al. | |
| 8,952,062 B2 | 2/2015 | Cook et al. | |
| 9,050,302 B2 | 6/2015 | Eller | |
| 9,226,910 B2 | 1/2016 | Khayrallah et al. | |
| 9,359,290 B2 | 6/2016 | Khayrallah et al. | |
| 9,610,274 B2 | 4/2017 | Lee et al. | |
| 2005/0080268 A1 | 4/2005 | Choi et al. | |
| 2005/0203130 A1 | 9/2005 | Buntinx | |
| 2008/0039529 A1 | 2/2008 | Sporn | |
| 2008/0090902 A1 | 4/2008 | Pandey et al. | |
| 2009/0312416 A1* | 12/2009 | Ahnaou | A61P 25/00 514/489 |
| 2010/0331332 A1 | 12/2010 | Lee et al. | |
| 2011/0111027 A1 | 5/2011 | Rourke et al. | |
| 2012/0004300 A1 | 1/2012 | Lee et al. | |
| 2012/0245226 A1 | 9/2012 | Lee et al. | |
| 2012/0252892 A1 | 10/2012 | Lee et al. | |
| 2014/0275244 A1 | 9/2014 | Khayrallah et al. | |
| 2014/0350098 A1 | 11/2014 | Ahnaou et al. | |
| 2015/0018414 A1 | 1/2015 | Khayrallah et al. | |

(Continued)

FOREIGN PATENT DOCUMENTS

| | | |
|---|---|---|
| EP | 0633023 | 1/1995 |
| JP | 9503231 | 3/1997 |
| WO | 9607637 | 3/1996 |

(Continued)

OTHER PUBLICATIONS

Ruoff et al. "Evaluation of the effect of JZP-110 in patients with narcolepsy assessed using the Maintenance of Wakefulness Test censored to 20 minutes", J. Sleep Med. 35:12-16 (2017) Epub Apr. 22, 2017.

Scrima et al. "Identifying clinically important difference on the Epworth Sleepiness Scale: results from a narcolepsy clinical trial of JZP-110", J. Sleep Med. 38:108-112 (2017) Epub Jul. 22, 2017.

Bogan et al. "Effect of oral JZP-110 (ADX-N05) treatment on wakefulness and sleepiness in adults with narcolepsy", Sleep Medicine 16(9):1102-1108 (2015).

Phenprobamate, Wikipedia, https://en.wikipedia.org/wiki/Phenprobamate, last edited Apr. 2, 2016, accessed Sep. 24, 2019.

Ruoff et al. "Effect of Oral JZP-110 (ADX-N05) on Wakefulness and Sleepiness in Adults with Narcolepsy: A Phase 2b Study", Sleep 39(7):1379-1387 (2016).

(Continued)

*Primary Examiner* — Sarah Pihonak
(74) *Attorney, Agent, or Firm* — Myers Bigel, P.A.

(57) ABSTRACT

The present invention relates to carbamoyl phenylalaninol compounds and methods of using the same to treat disorders. The invention further relates to the development of methods for treating excessive sleepiness in a subject, e.g., due to narcolepsy or obstructive sleep apnea, with the surprising outcome that "normal" levels of wakefulness are achieved based on standard objective and subjective sleepiness tests.

10 Claims, 14 Drawing Sheets

(56) References Cited

U.S. PATENT DOCUMENTS

| | | |
|---|---|---|
| 2015/0246874 A1 | 9/2015 | Kang et al. |
| 2016/0081970 A1 | 3/2016 | Khayrallah et al. |

FOREIGN PATENT DOCUMENTS

| | | |
|---|---|---|
| WO | 9624577 | 8/1996 |
| WO | 96032375 | 10/1996 |
| WO | 9815526 | 4/1998 |
| WO | 98017636 | 4/1998 |
| WO | 2006050037 | 5/2006 |
| WO | 2006133393 | 12/2006 |
| WO | 2007001841 | 1/2007 |
| WO | 2007018496 | 2/2007 |
| WO | 2008048801 | 4/2008 |
| WO | 2011005473 | 1/2011 |

OTHER PUBLICATIONS

Schweitzer et al. "A Phase 3, Randomized, Placebo-Controlled, Double-Blind, 12-Week, Multicenter Study of the Efficacy and Safety of JZP-110 for the Treatment of Excessive Sleepiness in Patients with Obstructive Sleep Apnea", Sleep 40:A237 (Abstract Supplement), 2017.

"Aulton, "Dissolution and solubility", Aug. 2, 2015, retrieved from https://clinicalgate.com/dissolution-and-solubility on May 13, 2018. (Year: 2015)".

"Diagnostic and Statistical Manual of Mental Disorders, Fourth Edition, Published by the American Psychiatric Association Washington, DC.".

"Fava, M. (2004) The Journal of Psychiatry, 65 (suppl16, 27-32)—abstract".

"Goodman & Gilman's The Pharmacological Basis of Therapeutics, Tenth Edition".

"Merck Manual, 1999, Symptoms and Signs, Treatment, p. 1415".

"Narcolepsy: Treatment Issues, Thomas Roth (J Clin Psychiatry 2007;68 [suppl 13]:16-19)".

"NovaScreen, dated: Oct. 24, 1994".

"SUPAC-IR: Immediate-Release Solid Oral Dosage Forms: Scale-Up and Post-Approval Changes: Chemistry, Manufacturing and Controls, In Vitro Dissolution Testing, and In Vivo Bioequivalence Documentation; Issued by: U.S. Department of Health and Human Services,".

Amsterdam, et al., ""A single-site, double-blind, placebo-controlled, dose-ranging study of YKP10A-a putative, new antidepressant", Progress in Neuro-Psychopharmacology & Biological Psychiatry 26:1333-1338 (2002)".

Amsterdam, et al., "Prog. Neuro-Psychopharmacol. Biol. Psychiatry 26:1333 (2002)".

Arnulf, et al., "(Neurology; Apr. 9, 2002, vol. 58, No. 7, 1 019-1 024)—abstract".

Black Je,, et al., ""Narcolepsy and syndromes of primary excessive daytime somnolence" seminars in Neurology 2004;24(3):271-262".

Gordon, et al., "Abstracts of the 28th Annual Meeting, Soc. NeuroSci. 24:1490 (1998)".

Hasan, et al., "Neuropsychopharmacology 34:1625 (2009)".

Lammers, et al., ", "Pharmacological management of narcolepsy", Expert Opin. Pharmacother. 2003 vol. 4 No. 10 pp. 1739-1746".

Poryazova, et al., ""Excessive Daytime Sleepiness in Parkinson's Disease: Characteristics and Determinants", Eur. Neurol. 63:129-135 (2010)".

Uzunovic, et al., ""Effect of Magnesium Stearate Concentration on Dissolution Properties of Ranitidine Hydrochloride Coated Tablets", Bosnian Journal of Basic Medical Sciences 7(3):279-283 (2007)".

U.S. Appl. No. 16/618,735; office action dated Jul. 29, 2020.

"Anonymous, ClinicalTrials.gov, NCT02348593, "Twelve-week Study of the Safety and Efficacy of JZP-110 in the Treatment of Excessive Sleepiness in Narcolepsy", Jul. 23, 2019".

"Anonymous, ClinicalTrials.gov, NCT02348606, "Twelve-week Study of the Safety and Efficacy of JZP-110 in the Treatment of Excessive Sleepiness in OSA" OSA, Jul. 23, 2019".

"Sunosi package insert Mar. 20, 2019".

Schweitzer, Paula K., et al., "Solriamfetol for Excessive Sleepiness in Obstructive Sleep Apnea (Tones 3) A Randomized Controlled Trial", American Journal of Respiratory and Critical Care Medicine 199(11):1421-1431 (Jun. 1, 2019).

Zomorodi, et al., "Poster 291, An Open-Label, Single-Dose, Phase 1 Study of the Pharmacokinetics and Safety of JZP-110 in Subjects with Normal or Impaired Renal Function and with End-Stage Renal Disease Requiring Hemodialysis" Sleep 2017, the 31st Annual Meeting of the Associate Professional Sleep Societies, Jun. 3-7, 2017.

Zomorodi, et al., "Poster T-038, Population Pharmacokinetic Analysis of Solriamfetol (JPZ-110), a Selective Dopamine and Norepinephrine Uptake Inhibitor", The Ninth American Conference on Pharmacometrics (ACoP9), Oct. 7-10, 2018.

Zomorodi, Katie, et al., "Single-Dose Pharmacokinetics and Safety of Solriamfetol in Participants With Normal or Impaired Renal Function and With End-Stage Renal Disease Requiring Hemodialysis", The Journal of Clinical Pharmacology 59(8):1120-1129 (2019).

* cited by examiner

METHODS AND COMPOSITIONS FOR TREATING EXCESSIVE SLEEPINESS

STATEMENT OF PRIORITY

This application is a continuation of and claims priority to U.S. patent application Ser. No. 16/618,735, filed Dec. 2, 2019, which is a 35 U.S.C. § 371 national phase application of PCT Application PCT/US2018/035532 filed Jun. 1, 2018, which claims the benefit, under 35 U.S.C. § 119(e), of U.S. Provisional Application No. 62/514,176, filed Jun. 2, 2017, the entire contents of each of which are incorporated by reference herein in its entirety.

FIELD OF THE INVENTION

The present invention relates to carbamoyl phenylalaninol compounds and methods of using the same to treat disorders.

BACKGROUND OF THE INVENTION (R)-2-amino-3-phenylpropyl carbamate (APC) is a phenylalanine analog that has been demonstrated to be useful in the treatment of a variety of disorders, including excessive daytime sleepiness, cataplexy, narcolepsy, fatigue, depression, bipolar disorder, fibromyalgia, and others. See, for example, U.S. Pat. Nos. 8,232,315; 8,440,715; 8,552,060; 8,623,913; 8,729,120; 8,741,950; 8,895,609; 8,927,602; 9,226,910; and 9,359,290; and U.S. Publication Nos. 2012/0004300 and 2015/0018414. The structure of the free base of APC is given below as formula I.

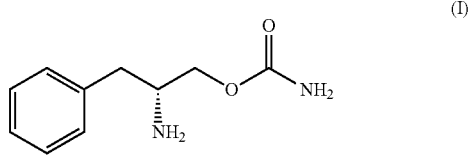 [SMILES: NC(=O)OC[C@H](N)Cc1ccccc1]

(I)

Methods for producing APC (which also has other names) and related compounds can be found in U.S. Pat. Nos. 5,955,499; 5,705,640; 6,140,532 and 5,756,817. All of the above patents and applications are hereby incorporated by reference in their entireties for all purposes.

While other compounds have been approved for the treatment of excessive sleepiness, few if any compounds have demonstrated the ability to improve the level of sleepiness in a subject to a level that is considered "normal" in sleepiness tests.

The present invention overcomes shortcomings in the art by providing methods and compositions for treating excessive sleepiness such that "normal" levels of wakefulness are achieved.

SUMMARY OF THE INVENTION

The present invention relates to the development of methods for treating excessive sleepiness in a subject, e.g., due to narcolepsy or obstructive sleep apnea, with the surprising outcome that "normal" levels of wakefulness are achieved based on standard objective and subjective sleepiness tests.

Accordingly, one aspect of the present invention relates to a method for treating excessive daytime sleepiness in a subject in need thereof, comprising administering to the subject (R)-2-amino-3-phenylpropyl carbamate or a pharmaceutically acceptable salt thereof in an amount sufficient to decrease the subject's score on the Epworth Sleepiness Scale (ESS) by 5 or more points, e.g., by 10 or more points. In some embodiments, the method is effective to decrease the subject's score on the ESS to a "normal" level, e.g., 10 or less.

Another aspect of the invention relates to a method for treating excessive daytime sleepiness in a subject in need thereof, comprising administering to the subject (R)-2-amino-3-phenylpropyl carbamate or a pharmaceutically acceptable salt thereof in an amount sufficient to increase the subject's score on the maintenance of wakefulness test (MWT) by at least 5 minutes, e.g., at least 10 minutes or 15 minutes.

A further aspect of the invention relates to a method for treating excessive daytime sleepiness in a subject in need thereof, comprising administering to the subject a therapeutically effective amount of (R)-2-amino-3-phenylpropyl carbamate or a pharmaceutically acceptable salt thereof no later than at least 12 hours before the bedtime of the subject.

The present invention is explained in greater detail in the drawings herein and the specification set forth below.

MCID, minimal clinically important difference; SE, standard error, SF-36v2, 36-item Short Form Health Survey version 2.

Figure 9:
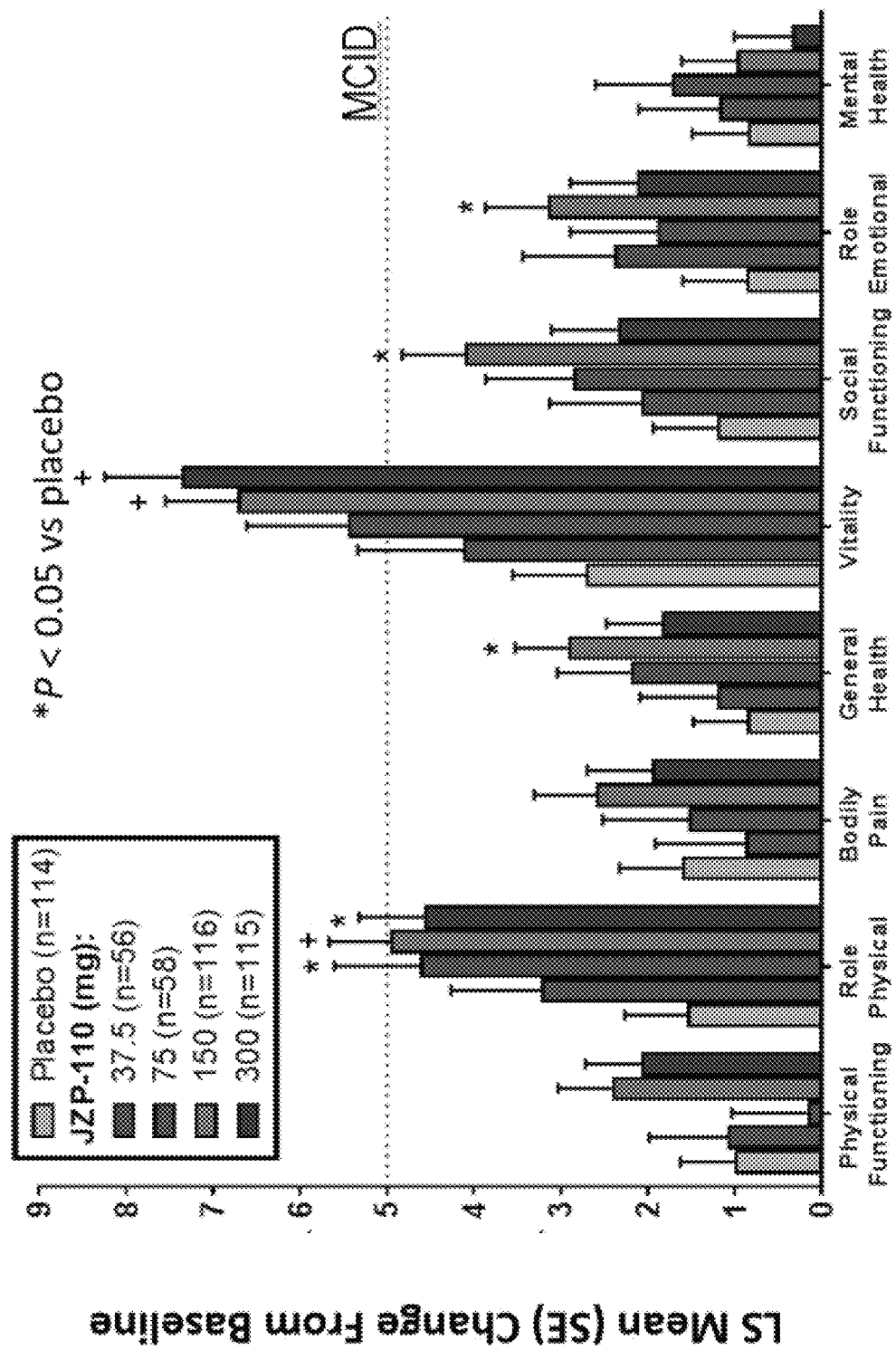

FIG. 9 shows the change from baseline at week 12 on individual SF-36 Domain Scores. Values are for the modified intent-to-treat population (n=459). Dashed horizontal line represents the MCID for a change in SF-36 score.[10] *P<0.05 vs. placebo. LS, least squares; MCID, minimal clinically important difference; MCS, Mental Component Summary; PCS, Physical Component Summary; SE, standard error; SF-36v2, 36-item Short Form Health Survey version 2.

Figures 10A, 10B:
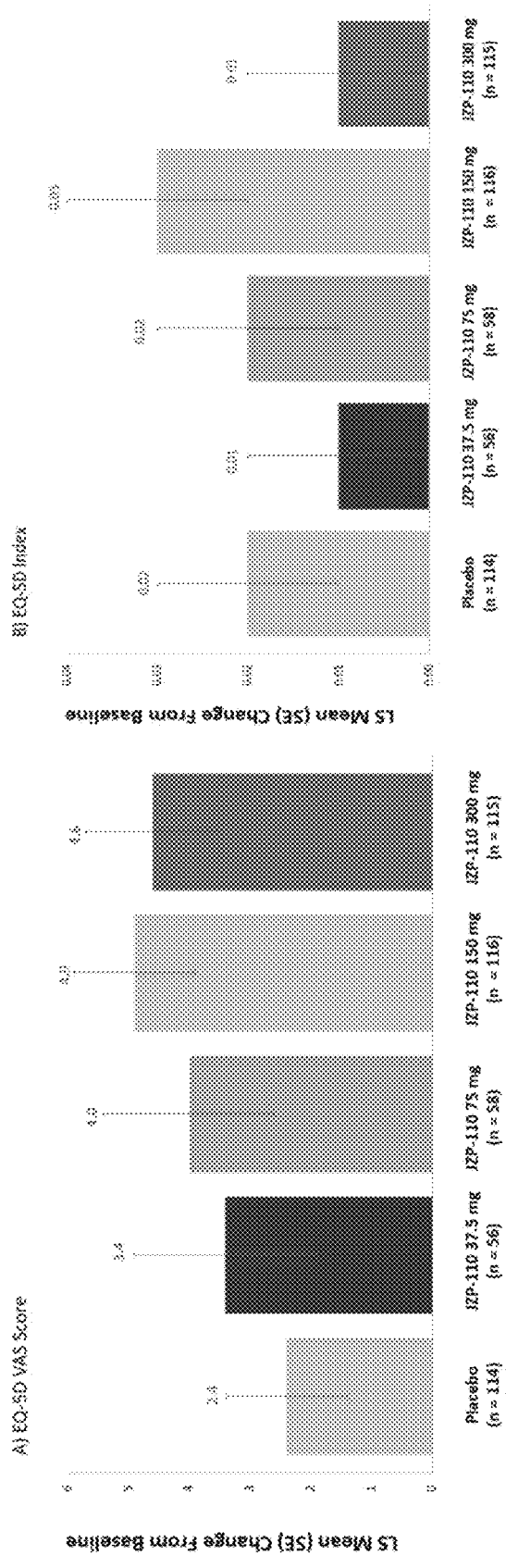

FIGS. 10A-10B show change from baseline at week 12 in EQ-5D-5L Scores. Values are for the modified intent-to-treat population (n=459). EQ-5D-5L, 5-dimension, 5-level EuroQol; LS, least squares; SE, standard error; VAS, visual analog scale.

Figure 11:
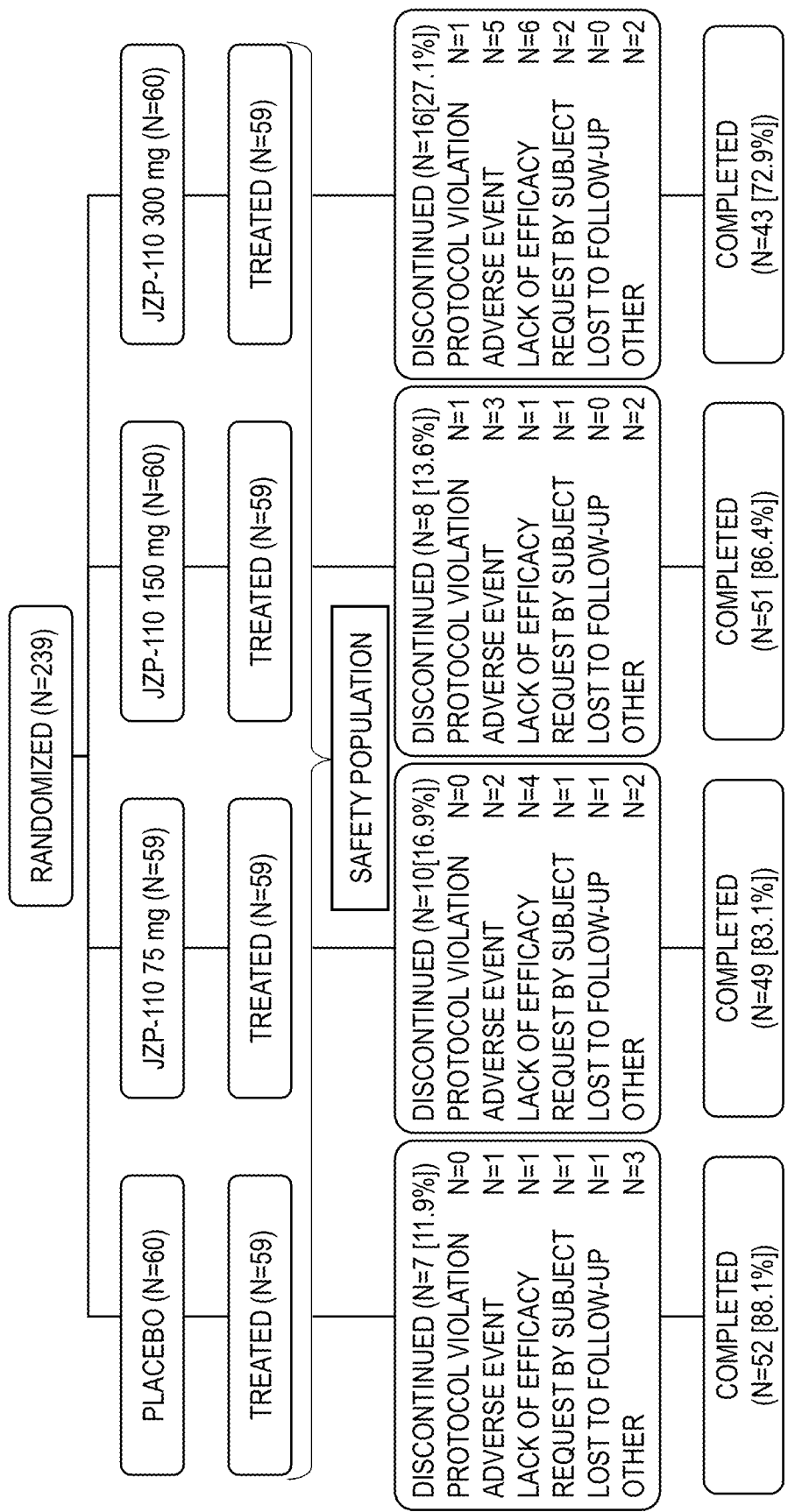

FIG. 11 shows patient disposition in the narcolepsy study.

Figure 12:
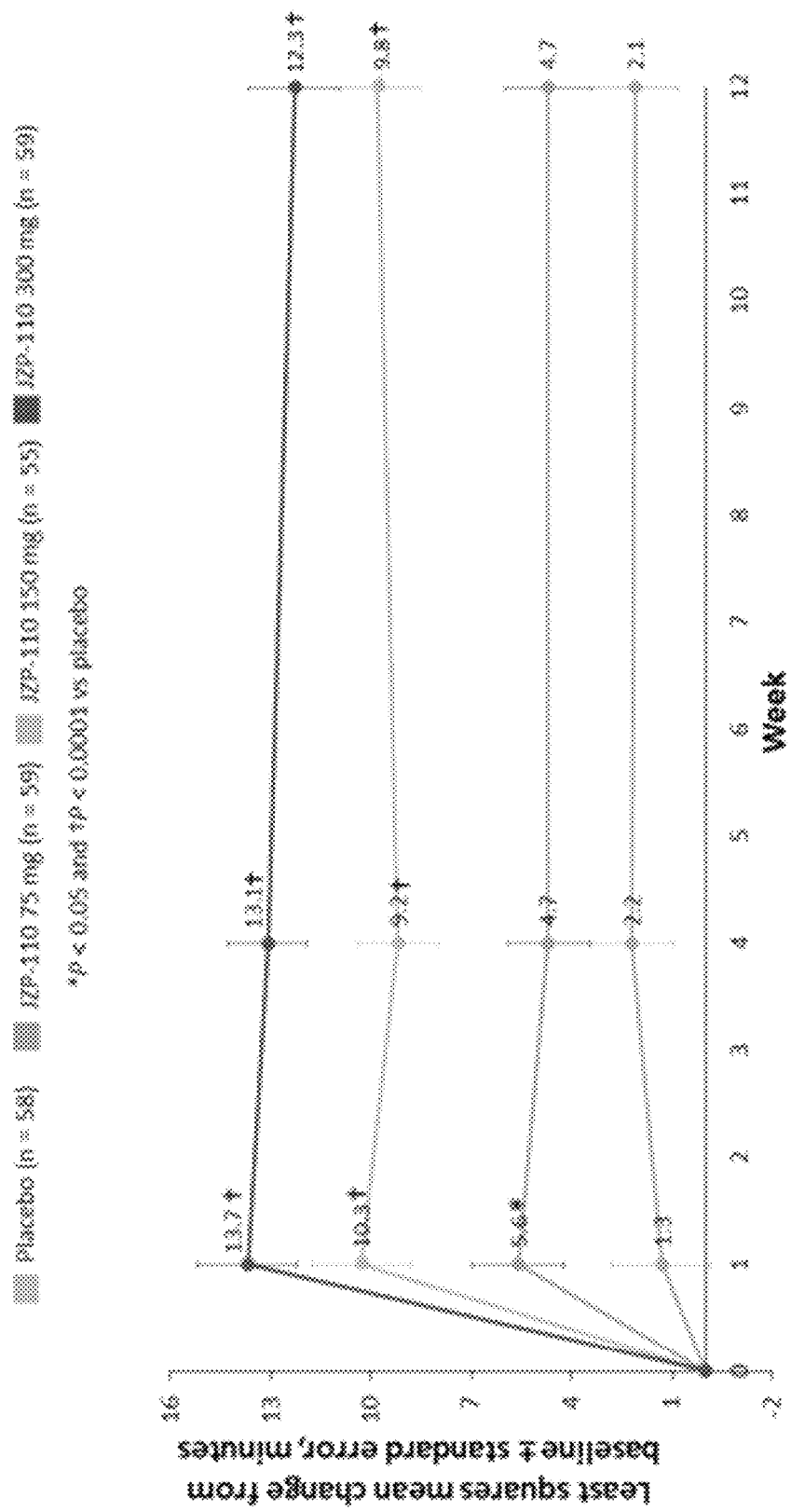

FIG. 12 shows mean change from baseline on the maintenance of wakefulness test.

Figure 13:
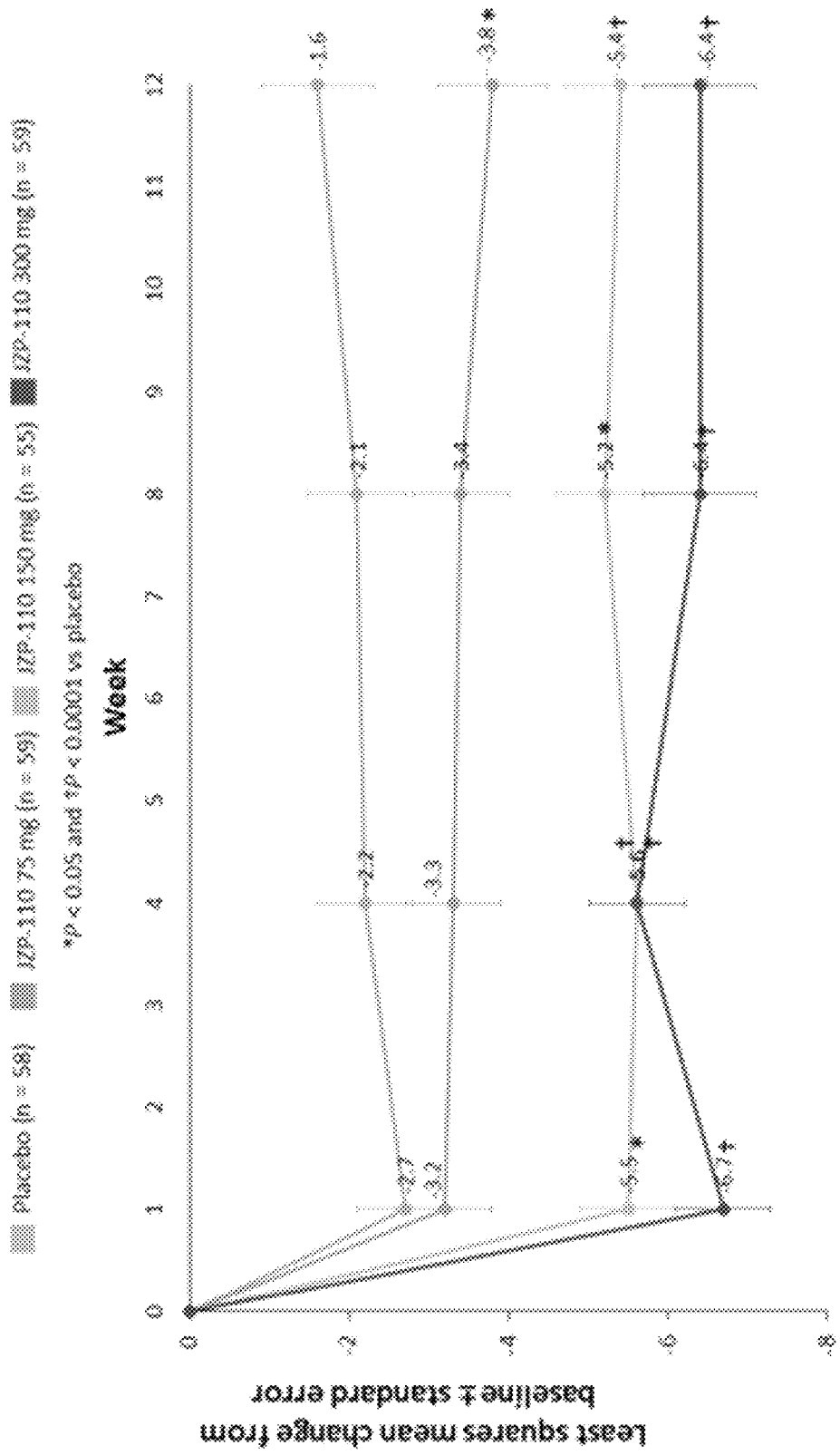

FIG. 13 shows mean change from baseline on the Epworth Sleepiness Scale.

Figure 14:
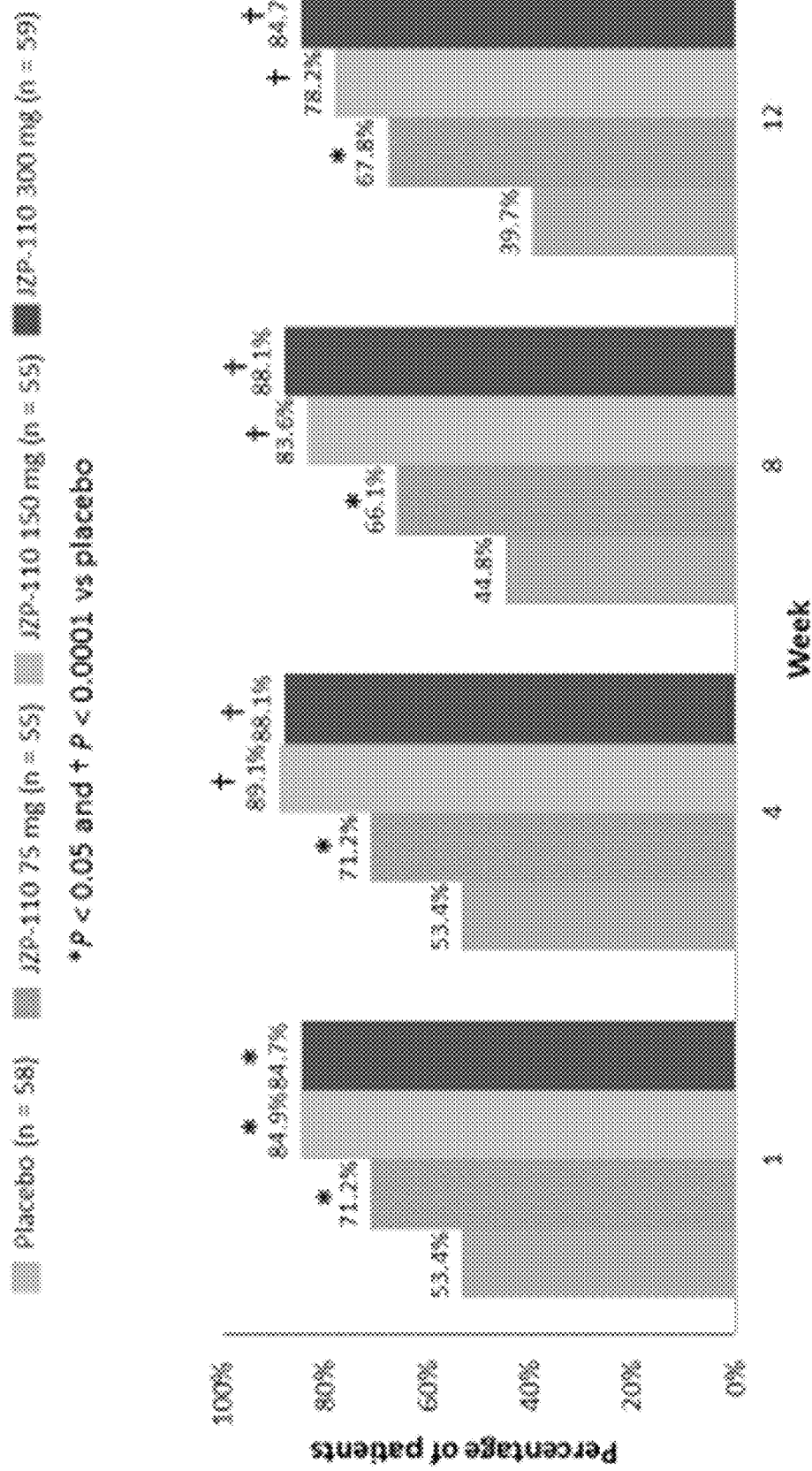

FIG. 14 shows the percentage of patients who reported improvement on the PGI-C Scale.

DETAILED DESCRIPTION OF THE INVENTION

The present invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

To illustrate, if the specification states that a complex comprises components A, B and C, it is specifically intended that any of A, B or C. or a combination thereof, can be omitted and disclaimed singularly or in any combination.

All publications, patent applications, patents, and other references mentioned herein are incorporated by reference herein in their entirety for all purposes.

As used herein, "a," "an," or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±10%, ±5%, ±1%, ±0.5%, or even ±0.1% of the specified amount.

The term "consists essentially of" (and grammatical variants), as applied to the compositions of this invention, means the composition can contain additional components as long as the additional components do not materially alter the composition. The term "materially altered," as applied to a composition, refers to an increase or decrease in the therapeutic effectiveness of the composition of at least about 20% or more as compared to the effectiveness of a composition consisting of the recited components.

The term "therapeutically effective amount" or "effective amount," as used herein, refers to that amount of a composition, compound, or agent of this invention that imparts a modulating effect, which, for example, can be a beneficial effect, to a subject afflicted with a disorder, disease or illness, including improvement in the condition of the subject (e.g., in one or more symptoms), delay or reduction in the progression of the condition, prevention or delay of the onset of the disorder, and/or change in clinical parameters, disease or illness, etc., as would be well known in the art. For example, a therapeutically effective amount or effective amount can refer to the amount of a composition, compound, or agent that improves a condition in a subject by at least 5%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 950%, or at least 100%.

"Treat" or "treating" or "treatment" refers to any type of action that imparts a modulating effect, which, for example, can be a beneficial effect, to a subject afflicted with a disorder, disease or illness, including improvement in the condition of the subject (e.g., in one or more symptoms), delay or reduction in the progression of the condition, and/or change in clinical parameters, disease or illness, etc., as would be well known in the art.

"Pharmaceutically acceptable," as used herein, means a material that is not biologically or otherwise undesirable, i.e., the material can be administered to an individual along with the compositions of this invention, without causing substantial deleterious biological effects or interacting in a deleterious manner with any of the other components of the composition in which it is contained. The material would naturally be selected to minimize any degradation of the active ingredient and to minimize any adverse side effects in the subject, as would be well known to one of skill in the art (see, e.g., *Remington's Pharmaceutical Science;* 21$^{st}$ ed. 2005).

"Concurrently" means sufficiently close in time to produce a combined effect (that is, concurrently can be simultaneously, or it can be two or more events occurring within a short time period before or after each other). In some embodiments, the administration of two or more compounds "concurrently" means that the two compounds are administered closely enough in time that the presence of one alters the biological effects of the other. The two compounds can be administered in the same or different formulations or sequentially. Concurrent administration can be carried out by mixing the compounds prior to administration, or by administering the compounds in two different formulations, for example, at the same point in time but at different anatomic sites or using different routes of administration.

A "disorder amenable to treatment with APC" refers to any disorder in which administration of APC to a subject results in the treatment of one or more symptoms of the disorder in the subject.

"Excessive daytime sleepiness" or "EDS" refers to persistent sleepiness at a time when the individual would be expected to be awake and alert, even during the day after apparently adequate or even prolonged nighttime sleep. EDS may be the result of a sleep disorder or a symptom of another underlying disorder such as narcolepsy, sleep apnea, circadian rhythm sleep disorder, or idiopathic hypersomnia. While the name includes "daytime," it is understood that the sleepiness may occur at other times that the subject should be awake, such as nighttime or other times, e.g., if the subject is working nightshift. It is also understood that EDS is medically distinct from fatigue and disorders associated with fatigue.

The present invention relates to a method for treating excessive daytime sleepiness in a subject in need thereof, comprising administering to the subject (R)-2-amino-3-phenylpropyl carbamate (APC) or a pharmaceutically acceptable salt thereof in an amount sufficient to decrease the subject's score on the Epworth Sleepiness Scale (ESS) by 5 or more points, e.g., by 10 or more points, e.g., by 1, 2, 3, 4, 5, 6, 7, 8, 9, 10, 11, 12, 13, 14, 15, 16, 17, 18, 19, or 20 or more points or any range therein. In some embodiments, the amount of PAC administered is sufficient to decrease the subject's score on the ESS to a level that is considered normal, e.g., 10 or less. In certain embodiments, at least about 5% of the treated subjects achieve the specified score, e.g., at least about 5%, 10%, 15%, 20%, 25%, 30%, 35%, 40%, 45%, 50%, 55%, 60%, 65%, 70%, 75%, 80%, 85%, 90%, 95%, or more.

The ESS is a subjective sleepiness test that is well known in the art and routinely used to measure the sleepiness level of a subject. The scale is intended to measure daytime sleepiness through the use of a short questionnaire that asks the subject to rate his or her probability of falling asleep on a scale of increasing probability from 0 to 3 for eight different situations that most people engage in during their daily lives. The scores for the eight questions are added together to obtain a single number that estimates the subject's average sleep propensity (ASP). A number in the 0-10 range is considered to be normal while 11-12 indicates mild excessive sleepiness, 13-15 indicates moderate excessive sleepiness, and 16 or higher indicates severe excessive sleepiness. Narcolepsy patients have an average score of about 17. Obstructive sleep apnea (OSA) patients with excessive sleepiness have an average score of about 15.

While certain drugs have been shown to improve excessive sleepiness in subjects and to improve ESS scores, it is unusual for a drug to improve the ESS score to the normal range, 10 or below. One of the unexpected advantages of the present invention is the ability, as demonstrated in clinical trials, to improve ESS scores in narcolepsy and OSA patients to 10 or below.

Another aspect of the invention relates to a method for treating excessive daytime sleepiness in a subject in need thereof, comprising administering to the subject (R)-2-amino-3-phenylpropyl carbamate or a pharmaceutically acceptable salt thereof in an amount sufficient to increase the subject's score on the maintenance of wakefulness test (MWT) by at least 5 minutes, e.g., at least 10 minutes or 15 minutes, e.g., at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 minutes or more or any range therein. In certain embodiments, at least about 5% of the treated subjects achieve the specified score, e.g., at least about 5%, 10%, 15%, 20%, 25%, 30%, 35%, 40%, 45%, 50%, 55%, 60%, 65%, 70%, 75%, 80%, 85%, 90%, 95%, or more.

The MWT is an objective test used to measure how alert a subject is during the day. The test consists of four sleep trials with two hours in between the trials. The first trial is performed 1.5-3 hours after the subject's normal wake-up time. Sensors are placed on the head, face, and chin to detect when the subject is asleep and awake during the test. The subject sits quietly in bed with his or her back and head supported by a pillow and is asked to sit still and look straight ahead while trying to stay awake as long as possible. Each trial lasts 40 minutes or until the subject is asleep for 90 seconds. Between trials, the subject stays out of bed and occupies himself or herself to remain awake. Falling asleep in an average of less than eight minutes is considered abnormal. About 40-60% of subjects with normal sleep stay awake for the entire 40 minutes of all four trials.

While certain drugs have been shown to improve excessive sleepiness in subjects and to improve MWT scores, it is unusual for a drug to improve the MWT score to the extent observed with the present invention.

The baseline measurement for determining a change in test results, such as ESS and MWT, may be performed before the subject has been administered APC or at a timepoint during a course of treatment of APC at which a baseline determination is desired. One or more subsequent determinations of test results may be made at any time after administration of one or more doses of APC. For example, determination of a change in test results may be made 1, 2, 3, 4, 5, or 6 days or 1, 2, 3, 4, 5, 6, 7, 8, 9, or 10 weeks after the administration of APC has begun or after the baseline determination was made.

A further aspect of the invention relates to a method for treating excessive daytime sleepiness in a subject in need thereof, comprising administering to the subject a therapeutically effective amount of (R)-2-amino-3-phenylpropyl carbamate or a pharmaceutically acceptable salt thereof no later than at least 12 hours before the bedtime of the subject. Studies by the present inventors have found that that administration of APC within a few hours of waking minimizes side effects of the treatment such as insomnia. In some embodiments, APC is administered shortly after waking. e.g., within about 0.25, 0.5, 0.75, 1, 1.5, 2, 2.5, or 3 hours of waking. It is preferable that, if APC is not administered first thing after waking, that it be administered at least 10 hours before the bedtime of the subject, e.g., at least 10, 11, 12, 13, 14, 15, or 16 or more hours before bedtime.

The methods of the invention may be effective no matter the cause of the EDS. In some embodiments, the cause of the EDS may be, without limitation, central nervous system (CNS) pathologic abnormalities, stroke, narcolepsy, idiopathic CNS hypersomnia; sleep deficiency, sleep apnea, obstructive sleep apnea, insufficient nocturnal sleep, chronic pain, acute pain, Parkinson's disease, urinary incontinence, multiple sclerosis fatigue, attention deficit hyperactivity disorder (ADHD), Alzheimer's disorder, major depression, bipolar disorder, cardiac ischemia misalignments of the body's circadian pacemaker with the environment, jet lag, shift work, or sedating drugs.

The methods of the invention may also be used to increase wakefulness and/or alertness in a subject in need thereof.

The methods of the present invention may be carried out using compounds, formulations and unit dosage forms provided herein. In some embodiments, the formulations and dosage forms can be utilized to achieve immediate release of APC, as well as pharmaceutically acceptable salts, hydrates, isomers, including tautomers, solvates and complexes of APC.

Suitable salts of APC include, without limitation, acetate, adipate, alginate, aspartate, benzoate, butyrate, citrate, fumarate, glycolate, hemisulfate, heptanoate, hexanoate, hydrochloride, hydrobromide, hydroiodide, 2-hydroxyethanesulfonate, lactate, maleate, malonate, methanesulfonate, nicotinate, nitrate, oxalate, palmoate, pectinate, persulfate, hydroxynapthoate, pivalate, propionate, salicylate, succinate, sulfate, tartrate, thiocyanate, tosylate and undecanoate. Other acids, such as oxalic, while not in themselves pharmaceutically acceptable, can be employed in the preparation of salts useful as intermediates in obtaining the compound of the invention and their pharmaceutically acceptable acid addition salts. In certain embodiments, the salt is the hydrochloride salt.

APC compounds include those having quaternization of any basic nitrogen-containing group therein.

The discussion herein is, for simplicity, provided without reference to stereoisomerism or the addition of deuterium atoms. Those skilled in the art will appreciate that APC can contain one or more asymmetric centers and thus occur as racemates and racemic mixtures and single optical isomers. All such isomeric and deuterated forms of these compounds are expressly included in the present invention.

The discussion herein is also provided without reference to polymorphs, hydrates, clathrates, solvates, inclusion compounds, isomers, or other forms of the compound. All such forms of APC are expressly included in the present invention.

Further, the compounds of the invention include prodrugs of the compounds that are converted to the active compound in vivo. For example, the compound can be modified to enhance cellular permeability (e.g., by esterification of polar groups) and then converted by cellular enzymes to produce the active agent. Methods of masking charged or reactive moieties as a pro-drug are known by those skilled in the art (see, e.g., P. Korgsgaard-Larsen and H. Bundgaard, A Textbook of Drug Design and Development, Reading U.K., Harwood Academic Publishers, 1991).

The term "prodrug" refers to compounds that are rapidly transformed in vivo to yield the parent compound of the above formula, for example, by hydrolysis in blood, see, e.g., T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299. Exemplary prodrugs include a prodrug that is metabolized in vivo by a subject to an active drug having an activity of the compounds as described herein, wherein the prodrug is an ester of an alcohol or carboxylic acid group, if such a group is present in the compound; an amide of an amine group or carboxylic acid group, if such groups are present in the compound; a urethane of an amine group, if such a group is present in the compound; an acetal or ketal of an alcohol group, if such a group is present in the compound; a N-Mannich base or an imine of an amine group, if such a group is present in the compound; or a Schiff base, oxime, acetal, enol ester, oxazolidine, or thiazolidine of a carbonyl group, if such a group is present in the compound, such as described, for example, in U.S. Pat. Nos. 6,680,324 and 6,680,322.

The term "pharmaceutically acceptable prodrug" (and like terms) as used herein refers to those prodrugs of APC which are, within the scope of sound medical judgment, suitable for use in contact with the tissues of humans and/or other animals without undue toxicity, irritation, allergic response and the like, commensurate with a reasonable risk/benefit ratio, and effective for their intended use, as well as the zwitterionic forms, where possible, of the compound of the invention.

APC or a pharmaceutically acceptable salt thereof may be obtained or synthesized by methods known in the art and as described herein. Details of reaction schemes for synthesizing APC have been described in U.S. Pat. Nos. 5,705,640; 5,756,817; 5,955,499; and 6,140,532, all incorporated herein by reference in their entirety.

Another aspect of the invention relates to a composition, e.g., a dosage form, comprising APC that is suitable for used in the methods of the invention. In some embodiments, the composition is a pharmaceutical composition comprising APC and a pharmaceutically acceptable carrier. In some embodiments, the dosage form is an oral dosage form, e.g., a tablet or a capsule, e.g., an immediate release dosage form.

In some embodiments, the dosage form is an immediate release tablet that releases at least 85%, e.g., at least 85%, 90%, 95%, 96%, 97%, 98%, or 99%, of the APC contained therein within a period of less than 15 minutes after administration of the tablet to a subject.

Formulations of APC, including immediate release formulations, may be processed into unit dosage forms suitable for oral administration, such as for example, filled capsules, compressed tablets or caplets, or other dosage form suitable for oral administration using conventional techniques. Immediate release dosage forms prepared as described may be adapted for oral administration, so as to attain and maintain a therapeutic level of the compound over a preselected interval. In certain embodiments, an immediate release dosage form as described herein may comprise a solid oral dosage form of any desired shape and size including round, oval, oblong cylindrical, or polygonal. In one such embodiment, the surfaces of the immediate release dosage form may be flat, round, concave, or convex.

In particular, when the immediate release formulations are prepared as a tablet, the immediate release tablets contain a relatively large percentage and absolute amount of the compound and so are expected to improve patient compliance and convenience, by replacing the need to ingest large amounts of liquids or liquid/solid suspensions. One or more immediate release tablets as described herein can be administered, by oral ingestion, e.g., closely spaced, in order to provide a therapeutically effective dose of the compound to the subject in a relatively short period of time.

Where desired or necessary, the outer surface of an immediate release dosage form may be coated, e.g., with a color coat or with a moisture barrier layer using materials and methods known in the art.

In some embodiments, the composition is an immediate release compressed tablet, the tablet comprising:
APC or a pharmaceutically acceptable salt thereof in an amount of about 90-98% by weight of the tablet;
at least one binder in an amount of about 1-5% by weight of the tablet; and
at least one lubricant in an amount of about 0.1-2% by weight of the tablet;
wherein the tablet releases at least 85% of the APC or a pharmaceutically acceptable salt thereof contained therein within a period of less than 15 minutes after administration of the tablet to a subject.

In one embodiment, the tablet comprises:
APC or a pharmaceutically acceptable salt thereof in an amount of about 91-95% by weight of the tablet;
at least one binder in an amount of about 2-3% by weight of the tablet;
at least one lubricant in an amount of about 0.1-1% by weight of the tablet; and
optionally, a cosmetic film coat in an amount of about 3-4% by weight of the tablet;
wherein the tablet releases at least 85% of the APC or a pharmaceutically acceptable salt thereof contained therein within a period of less than 15 minutes after administration of the tablet to a subject.

In one embodiment, the tablet comprises:
APC or a pharmaceutically acceptable salt thereof in an amount of about 93.22% by weight of the tablet;
at least one binder (e.g., hydroxypropylcellulose) in an amount of about 2.87% by weight of the tablet;
at least one lubricant (e.g., magnesium stearate) in an amount of about 0.52% by weight of the tablet; and
optionally, a cosmetic film coat (e.g., Opadry® II yellow) in an amount of about 3-4% by weight of the tablet;
wherein the tablet releases at least 85% of the APC or a pharmaceutically acceptable salt thereof contained therein within a period of less than 15 minutes after administration of the tablet to a subject.

In some embodiments, the composition is an immediate release oral dosage form of APC, the oral dosage form comprising:
APC or a pharmaceutically acceptable salt thereof in an amount of about 90-98% by weight of the oral dosage form;
at least one binder in an amount of about 1-5% by weight of the oral dosage form; and
at least one lubricant in an amount of about 0.1-2% by weight of the oral dosage form;
wherein the oral dosage form releases at least 85% of the APC or a pharmaceutically acceptable salt thereof contained therein within a period of less than 15 minutes after administration of the oral dosage form to a subject.

In certain embodiments, the tablet does not comprise a disintegrant. The term "disintegrant," as used herein, refers to an agent added to a tablet to promote the breakup of the tablet in an aqueous environment. The tablets of the present invention are advantageous in that they dissolve rather than disintegrate. In the present invention the presence of disintegrant in the formulation may actually slow down release of APC.

In certain embodiments, APC or a pharmaceutically acceptable salt thereof is present in an amount of about 90%, 90.5%, 91%, 91.5%, 92%, 92.5%, 93%, 93.5%, 94%, 94.5%, 95%, 95.5%, 96%, 96.5%, 97%, 97.5%, or 98% by weight of the tablet or any value or range therein. In certain embodiments, APC or a pharmaceutically acceptable salt thereof is present in an amount of about 90% to about 98%, about 92% to about 98%, about 94% to about 98%, about 96% to about 98%, about 90% to about 92%, about 90% to about 94%, about 90% to about 96%, about 92% to about 94%, about 92% to about 96%, or about 94% to about 96%.

In certain embodiments, the at least one binder is present in an amount of about 1%, 1.5%, 2%, 2.5%, 3%, 3.5%, 4%, 4.5%, or 5% by weight of the tablet or any value or range therein. In certain embodiments, the at least one binder is present in an amount of about 1% to about 5%, about 2% to about 5%, about 3% to about 5%, about 4% to about 5%, about 1% to about 2%, about 1% to about 3%, about 1% to about 4%, about 2% to about 3%, about 2% to about 4%, or about 3% to about 4%. The tablet may comprise at least one binder, e.g., 1, 2, 3, 4, 5, or more binders.

In certain embodiments, the at least one binder is selected from at least one of hydroxypropyl cellulose, ethylcellulose, hydroxypropyl methylcellulose, polyvinyl alcohol, hydroxyethyl cellulose, povidone, copovidone, pregelatinized starch, dextrin, gelatin, maltodextrin, starch, zein, acacia, alginic acid, carbomers (cross-linked polyacrylates), polymethacrylates, sodium carboxymethylcellulose, guar gum, hydrogenated vegetable oil (type 1), methylcellulose, magnesium aluminum silicate, and sodium alginate or any combination thereof. In some embodiments, the at least one binder is hydroxypropyl cellulose.

In certain embodiments, the at least one lubricant is present in an amount of about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, or 2.0% by weight of the tablet or any value or range therein. In certain embodiments, the at least one lubricant is present in an amount of about 0.1% to about 2.0%, about 0.5% to about 2.0%, about 1.0% to about 2.0%, about 1.5% to about 2.0%, about 0.1% to about 0.5%, about 0.1% to about 1.0%, about 0.1% to about 1.5%, about 0.5% to about 1.0%, about 0.5% to about 1.5%, or about 1.0% to about 1.5%. The tablet may comprise at least one lubricant, e.g., 1, 2, 3, 4, 5, or more lubricants. Where the immediate release formulation is provided as a tableted dosage form, still lower lubricant levels may be achieved with use of a "puffer" system during tableting. Such systems are known in the art, commercially available and apply lubricant directly to the punch and die surfaces rather than throughout the formulation.

In certain embodiments, the at least one lubricant is selected from at least one of magnesium stearate, stearic acid, calcium stearate, hydrogenated castor oil, hydrogenated vegetable oil, light mineral oil, magnesium stearate, mineral oil, polyethylene glycol, sodium benzoate, sodium stearyl fumarate, and zinc stearate or any combination thereof. In some embodiments, the at least one lubricant is magnesium stearate. In other embodiments, magnesium stearate may be used in combination with one or more other lubricants or a surfactant, such as sodium lauryl sulfate. In particular, if needed to overcome potential hydrophobic properties of magnesium stearate, sodium lauryl sulfate may also be included when using magnesium stearate (Remington: the Science and Practice of Pharmacy, $20^{th}$ edition, Gennaro. Ed., Lippincott Williams & Wilkins (2000)).

In some embodiments, the at least one binder is hydroxypropyl cellulose. In some embodiments, the at least one lubricant is magnesium stearate. In some embodiments, the at least one binder is hydroxypropyl cellulose and the at least one lubricant is magnesium stearate.

In certain embodiments, the tablet is coated. The coating may be, without limitation, a color overcoat.

In some embodiments, the APC or a pharmaceutically acceptable salt thereof is APC hydrochloride.

The tablet may be any shape that is suitable for immediate release and allows the release of at least 85% of the APC or a pharmaceutically acceptable salt thereof contained therein within a period of less than 15 minutes after administration of the tablet to a subject. In some embodiments, the tablet maximizes surface area to volume ratio to promote rapid dissolution. In some embodiments, the tablet is oblong in shape.

The tablet may contain any amount of APC or a pharmaceutically acceptable salt thereof suitable for administration as a unit dosage form. In some embodiments, the tablet contains about 1 mg to about 1000 mg of the drug or any range or value therein, e.g., about 100 mg to about 500 mg, e.g., about 37.5 mg, about 75 mg, about 150 mg, or about 300 mg.

"Immediate release" as used herein, refers to a composition that releases APC or a pharmaceutically acceptable salt, hydrate, isomer, tautomer, solvate or complex thereof substantially completely into the gastrointestinal tract of the user within a period of less than about 15 minutes, usually between about 1 minute and about 15 minutes from ingestion. Such a delivery rate allows the drug to be absorbed by the gastrointestinal tract in a manner that is bioequivalent to an oral solution. Such rapid absorption will typically occur for an immediate release unit dosage form, such as a tablet, caplet or capsule, if the drug included in such dosage form dissolves in the upper portion the gastrointestinal tract.

Release rates can be measured using standard dissolution test methods. For example, the standard conditions may be those described in FDA guidance (e.g., 50 rpm, 37° C., USP 2 paddles, pH 1.2 and pH 6.8 media, 900 ml, 1 test article per vessel).

Immediate release formulations suitable for oral administration may comprise unit dosage forms, such as tablets, caplets or filled capsules, which can deliver a therapeutically effective dose of APC upon ingestion thereof by the patient of one or more of said dosage forms, each of which can provide a dosage of, for example, about 1 to about 1000 mg of APC. Additionally, the immediate release dosage forms can be shaped or scored to facilitate dose adjustment through tablet splitting.

The formulation and structure of an immediate release dosage form as disclosed herein can be adjusted to provide immediate release performance that suits a particular dosing need. In particular, the formulation and structure of the dosage forms as described herein can be adjusted to provide any combination of the immediate release performance characteristics described herein. In particular embodiments, for example, an immediate release dosage form as disclosed herein provides rapid onset of action, releasing more than about 85%, such as, for example, more than about 90% or 95%, of the drug contained therein within a period of time selected from less than 15 minutes, less than 12 minutes, less than 10 minutes, and less than 5 minutes after administration.

Moreover, the rate of drug release from an immediate release dosage form as disclosed herein may be adjusted as needed to facilitate a desired dosing regimen or achieve targeted dosing. In one embodiment, the immediate release dosage form may be formulated to deliver as much as 1,000 mg of APC. In particular embodiments, the total amount of drug contained within an immediate release dosage form according to the present description may be between about 50 mg and about 500 mg. For example, in certain such embodiments, the total amount of drug may be selected from about 10, 20, 30, 40, 50, 60, 70, 80, 90, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or 1000 mg or any range or value therein. In certain such embodiments, the total amount of drug may be about 10 mg to about 1000 mg, about 10 mg to about 500 mg, about 10 mg to about 300 mg, about 30 mg to about 1000 mg, about 30 mg to about 500 mg, about 30 mg to about 300 mg, about 100 mg to about 1000 mg, about 10 mg to about 500 mg, about 100 mg to about 300 mg, about 150 mg to about 1000 mg, about 150 mg to about 500 mg, or about 150 mg to about 300 mg.

The immediate release formulations provided herein generally include APC and some level of lubricant to facilitate processing of the formulations into a unit dosage form. In some embodiments, therefore, the formulations described herein include a combination of APC and lubricant, as described herein, and in certain such embodiments, the immediate release formulations are substantially free of other excipients or adjuvants. In other embodiments, the immediate release formulations described herein include a combination of APC, lubricant, and binder, as described herein, and in certain such embodiments, the immediate release formulations are substantially free of other excipients or adjuvants. Though the immediate release formulations described herein may be formulated using a combination of drug and one or more of a lubricant and binder, in certain embodiments, the compositions described herein may include one or more additional excipients selected from, for example, fillers, compression aids, diluents, disintegrants, colorants, flavorants, buffering agents, coatings, glidants, or other suitable excipients.

The immediate release formulations described herein may be manufactured using standard techniques, such as wet granulation, roller compaction, fluid bed granulation, and dry powder blending. Suitable methods for the manufacture of the immediate release formulations and unit dosage forms described herein are provided, for example, in Remington, $20^{th}$ edition, Chapter 45 (Oral Solid Dosage Forms). It has been found that, even without the aid of binders or non-lubricating excipients, such as compression aids, wet granulation techniques can afford flowable granules with compression characteristics suitable for forming unit dosage forms as described herein. Therefore, in certain embodiments, where a drug content greater than about 85%, 90% or 95% by weight is desired for the immediate release formulation, wet granulation techniques may be used to prepare immediate release formulations as described herein. In such embodiments, as illustrated in the Examples provided herein, conventional organic or aqueous solvents may be used in the wet granulation process. Suitable wet granulation processes can be performed as fluidized bed, high shear, or low shear (wet massing) granulation techniques, as are known in the art.

In addition to one or more of APC, lubricant, and binder, where desired, the immediate release formulations described herein may also include fillers or compression aids selected from at least one of lactose, calcium carbonate, calcium sulfate, compressible sugars, dextrates, dextrin, dextrose, kaolin, magnesium carbonate, magnesium oxide, maltodextrin, mannitol, microcrystalline cellulose, powdered cellulose, and sucrose. Where a filler or compression aid is used, in certain embodiments, it may be included in the immediate release formulation in an amount ranging from about 1%-15% by weight.

Immediate release formulations as described herein may be processed into unit dosage forms suitable for oral administration, such as for example, filled capsules, compressed tablets or caplets, or other dosage form suitable for oral administration using conventional techniques. Immediate release dosage forms prepared as described may be adapted for oral administration, so as to attain and maintain a therapeutic level of APC over a preselected interval. In certain embodiments, an immediate release dosage form as described herein may comprise a solid oral dosage form of any desired shape and size including round, oval, oblong, cylindrical, or polygonal. In one such embodiment, the surfaces of the immediate release dosage form may be flat, round, concave, or convex. In some embodiments, the shape may be selected to maximize surface area, e.g., to increase the rate of dissolution of the dosage form.

In particular, when the immediate release formulations are prepared as a tablet, the immediate release tablets contain a relatively large percentage and absolute amount of APC and so are expected to improve patient compliance and convenience, by replacing the need to ingest large amounts of liquids or liquid/solid suspensions. One or more immediate release tablets as described herein can be administered, by oral ingestion, e.g., closely spaced, in order to provide a therapeutically effective dose of APC to the subject in a relatively short period of time. For example, dissolution of a 10 mg-1000 mg tablet prepared according to the present description can provide about 80-100% of the APC to the subject in about 10-15 minutes.

Where desired or necessary, the outer surface of an immediate release dosage form as disclosed herein may be coated with a moisture barrier layer using materials and methods known in the art. For example, where the APC delivered by the unit dosage form is highly hygroscopic, providing a moisture barrier layer over the immediate release dosage form as disclosed herein may be desirable. For example, protection of an immediate release dosage form as disclosed herein from water during storage may be provided or enhanced by coating the tablet with a coating of a substantially water soluble or insoluble polymer. Useful water-insoluble or water-resistant coating polymers include ethyl cellulose and polyvinyl acetates. Further water-insoluble or water resistant coating polymers include polyacrylates, polymethacrylates or the like. Suitable water-soluble polymers include polyvinyl alcohol and HPMC. Further suitable water-soluble polymers include PVP, HPC, HPEC, PEG, HEC and the like.

Where desired or necessary, the outer surface of an immediate release dosage form as disclosed herein may be coated with a color overcoat or other aesthetic or functional layer using materials and methods known in the art.

The dosage forms disclosed herein can also be provided as a kit comprising, separately packaged, a container comprising a plurality of immediate release tablets, which tablets can be individually packaged, as in foil envelopes or in a blister pack. The tablets can be packaged in many conformations with or without desiccants or other materials to prevent ingress of water. Instruction materials or means, such as printed labeling, can also be included for their administration, e.g., sequentially over a preselected time period and/or at preselected intervals, to yield the desired levels of APC in vivo for preselected periods of time, to treat a preselected condition.

A daily dose of about 1 to about 2000 mg of APC or a pharmaceutically acceptable salt thereof may be administered to accomplish the therapeutic results disclosed herein. For example, a daily dosage of about 10-1000 mg, e.g., about 20-500 mg, in single or divided doses, is administered. In some embodiments, the daily dose may be about 0.01 to about 150 mg/kg body weight, e.g., about 0.2 to about 18 mg/kg body weight.

In one embodiment of the invention, APC is administered to the subject as needed to treat a disorder. The compound can be administered continuously or intermittently. In one embodiment, the compound is administered to the subject more than once a day, e.g., 2, 3, or 4 times per day, or once every 1, 2, 3, 4, 5, 6, or 7 days. In another embodiment, the compound is administered to the subject no more than once a week, e.g., no more than once every two weeks, once a month, once every two months, once every three months, once every four months, once every five months, once every six months, or longer. In a further embodiment, the compound is administered using two or more different schedules. e.g., more frequently initially (for example to build up to a certain level, e.g., once a day or more) and then less frequently (e.g., once a week or less). In other embodiments, the compound can be administered by any discontinuous administration regimen. In one example, the compound can be administered not more than once every three days, every four days, every five days, every six days, every seven days, every eight days, every nine days, or every ten days, or longer. The administration can continue for one, two, three, or four weeks or one, two, or three months, or longer. Optionally, after a period of rest, the compound can be administered under the same or a different schedule. The period of rest can be one, two, three, or four weeks, or longer, according to the pharmacodynamic effects of the compound on the subject. In another embodiment the compound can be administered to build up to a certain level, then maintained at a constant level and then a tailing dosage.

In one aspect of the invention, APC is delivered to a subject concurrently with an additional therapeutic agent. The additional therapeutic agent can be delivered in the same composition as the compound or in a separate composition. The additional therapeutic agent can be delivered to the subject on a different schedule or by a different route as compared to the compound. The additional therapeutic agent can be any agent that provides a benefit to the subject. Further agents include, without limitation, stimulants, anti-psychotics, anti-depressants, agents for neurological disorders, and chemotherapeutic agents. One therapeutic agent that can be administered during the same period is Xyrem®, sold commercially by Jazz Pharmaceuticals, which is used to treat narcolepsy and cataplexy. See U.S. Pat. Nos. 8,952,062 and 9,050,302.

The present invention finds use in research as well as veterinary and medical applications. Suitable subjects are generally mammalian subjects. The term "mammal" as used herein includes, but is not limited to, humans, non-human primates, cattle, sheep, goats, pigs, horses, cats, dog, rabbits, rodents (e.g., rats or mice), etc. Human subjects include neonates, infants, juveniles, adults and geriatric subjects.

In particular embodiments, the subject is a human subject that has excessive daytime sleepiness or another disorder amenable to treatment with APC. In other embodiments, the subject used in the methods of the invention is an animal model of excessive daytime sleepiness or another disorder amenable to treatment with APC.

The subject can be a subject "in need of" the methods of the present invention, e.g., in need of the therapeutic effects of the inventive methods. For example, the subject can be a subject that is experiencing excessive daytime sleepiness or another disorder amenable to treatment with APC, is suspected of having excessive daytime sleepiness or another disorder amenable to treatment with APC, and/or is anticipated to experience excessive daytime sleepiness or another disorder amenable to treatment with APC, and the methods and compositions of the invention are used for therapeutic and/or prophylactic treatment.

The present invention is explained in greater detail in the following non-limiting Examples. Each example has a self-contained list of references.

Example 1

Phase 3 Study of the Safety and Efficacy of APC for the Treatment of Excessive Sleepiness in Subjects with Obstructive Sleep Apnea Excessive sleepiness (ES) is one of the main presenting complaints in obstructive sleep apnea (OSA) and is estimated to persist in 62.5% of patients, despite being compliant with continuous positive airway pressure (CPAP) therapy (Weaver et al., *Sleep* 30(6):711 (2007)). ES in OSA contributes to reductions in function and work productivity (Nena et al., *J. Occup. Environ. Med.* 52(6):622 (2010); Hirsch Allen et al., *Chest* 147(5):1422 (2015)), and is associated with a higher risk of motor and occupational accidents (Garbarino et al., *Sleep* 39(6):1211 (2016); Rodenstein, *Respiration* 78(3):241 (2009)). APC is a selective dopamine and norepinephrine reuptake inhibitor with robust wake-promoting effects in nonclinical models and phase 2 clinical trials in patients with narcolepsy (Bogan et al., *Sleep Med.* 16(9):1102 (2015); Ruoff et al., *Sleep* 39(7):1379 (2016)). This study evaluated the safety and maintenance of efficacy of APC hydrochloride (JZP-110) administered once daily compared with placebo for the treatment of ES in adults with OSA.

Figure 1:
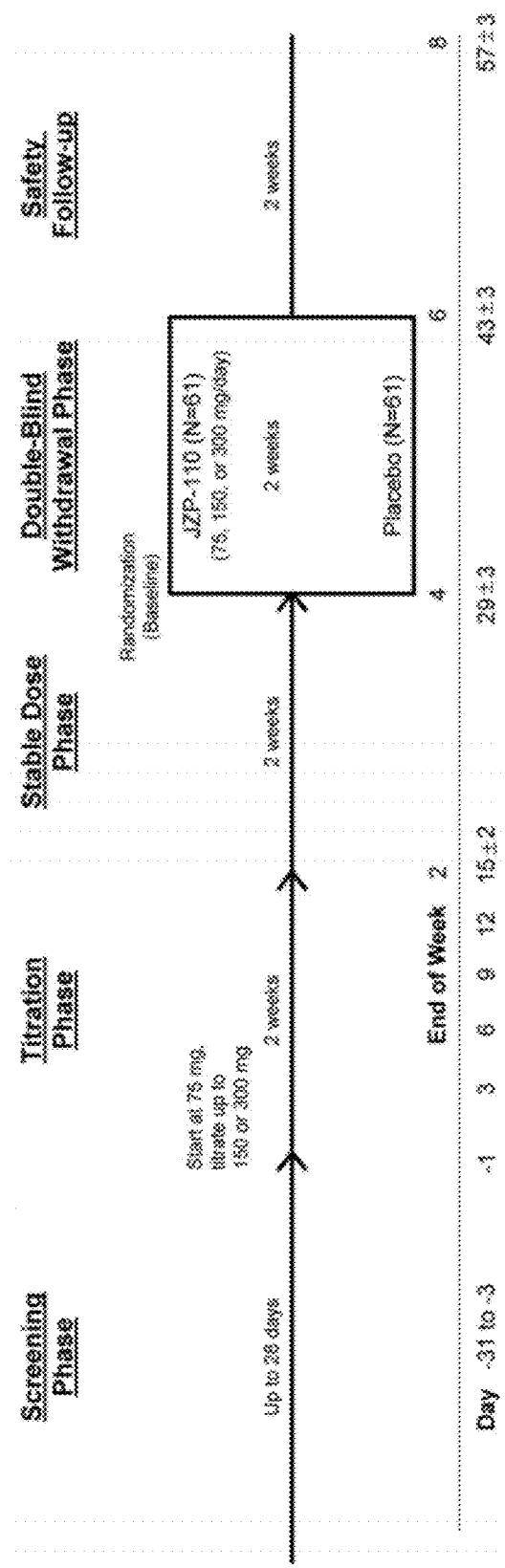
FIG. 1 shows the study design for treatment of excessive sleepiness in patients with obstructive sleep apnea.

The study was a double-blind, placebo-controlled, enriched, randomized withdrawal design (FIG. 1). In the Titration Phase (weeks 1-2), patients started on a once-daily dose of APC 75 mg and could be titrated up or down every 3 days to reach a maximum tolerated dose of APC 75, 150, or 300 mg. In the Stable-Dose Phase (weeks 3-4), patients continued to receive the dose that they were titrated to in the Titration Phase for 2 weeks. In the Double-Blind Withdrawal Phase (weeks 5-6), patients who reported "much" or "very much" improvement on the Patient Global Impression of Change (PGI-C) scale (Guy W. *ECDEU assessment manual for psychopharmacology, revised*. US Department of Health, Education, and Welfare publication (ADM 76-338). Rockville, Md.: National Institute of Mental Health; 1976), and who had improved on the Maintenance of Wakefulness Test (MWT) and Epworth Sleepiness Scale (ESS) (Johns, *Sleep* 14(6):540 (1991)) at week 4 were randomized 1:1 to receive the same current dose of JZP-110 or placebo for 2 weeks.

Key inclusion criteria included adults (18-75 years) with OSA diagnosed according to *International Classification of Sleep Disorders-3 Criteria* (American Academy of Sleep Medicine. *The International Classification of Sleep Disorders—Third Edition (ICSD-3)*. Darien, Ill.: American Academy of Sleep Medicine; 2014) along with current or prior use of a primary OSA therapy including CPAP, oral appliance, or surgical intervention, baseline score ≥10 on the Epworth Sleepiness Scale (ESS) (Johns, *Sleep* 14(6):540 (1991)) and MWT mean sleep latency <30 minutes on the first 4 trials of a 5-trial, 40-minute MWT, and Usual nightly sleep time ≥6 hours.

Key exclusion criteria included ES due to a cause other than OSA, occupation requiring nighttime- or variable-shift work, medical condition or history that could affect patient safety or interfere with study assessments, and recent use of any over-the-counter or prescription medications that could affect the evaluation of ES.

Efficacy was based on change from week 4 to 6 on the co-primary endpoints of MWT and ESS and percentage of patients reported as improved on the PGI-C and Clinician Global Impression of Change (CGI-C); assessed on a 7-point scale from 1 (very much improved) to 7 (very much worse).

MWT and ESS data were analyzed using a mixed-effect model repeated measures (MMRM); PGI-C and CGI-C were evaluated using a chi-square test. Efficacy analyses were performed on the modified intent-to-treat (mITT) population (patients who were randomized, received ≥1 dose of study medication, and had a week 4 and ≥1 post-week 4 MWT or ESS assessment); analysis of covariance was used for the co-primary endpoints, with treatment group, measurement at week 4, and randomization stratification factor as fixed effects. Safety and tolerability were evaluated based on treatment-emergent adverse events (TEAEs), vital signs, and laboratory values.

Figure 2:
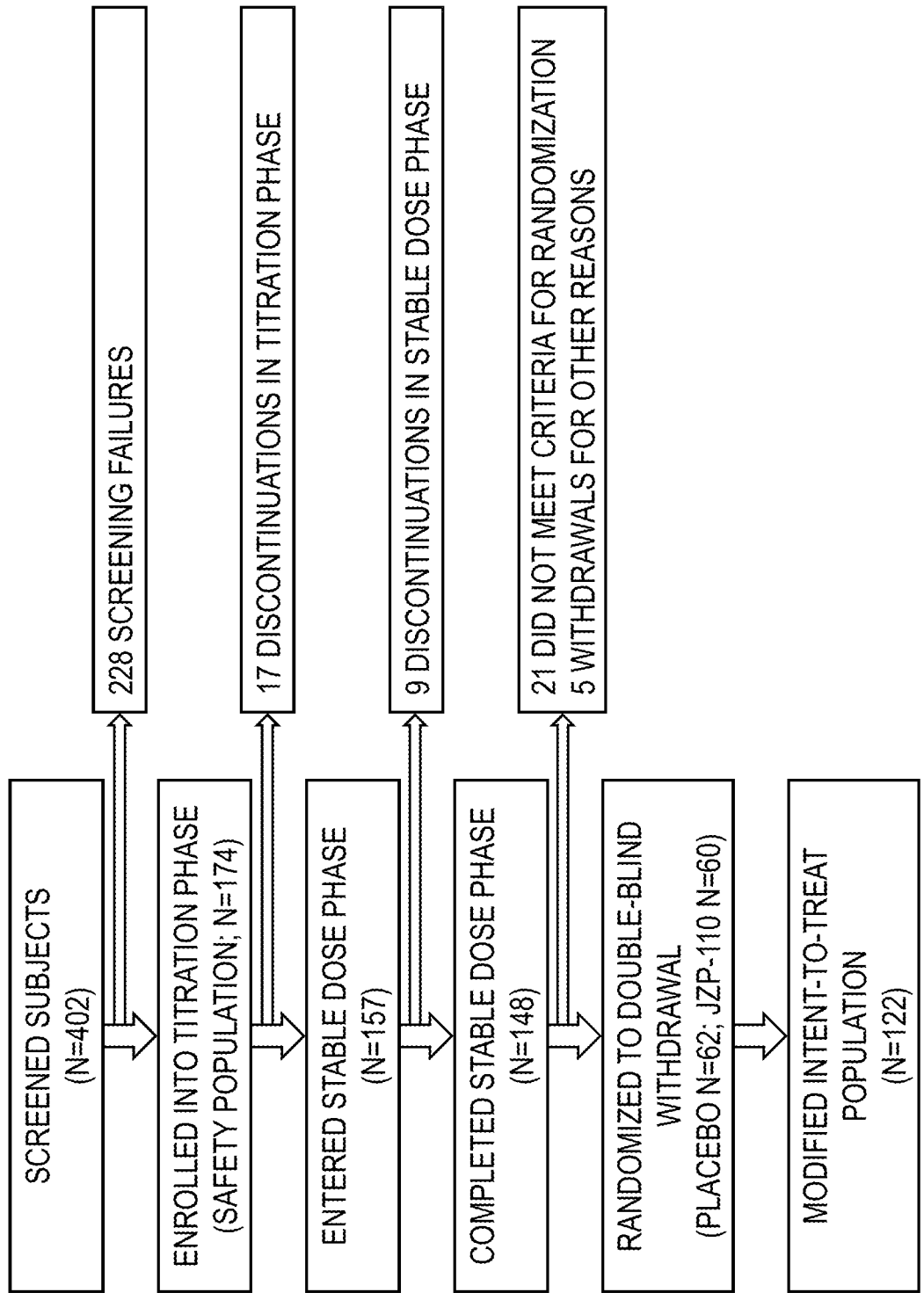
FIG. 2 shows patient disposition through the three study phases.

Of the 402 patients who were screened, 174 were enrolled in the Titration Phase, received ≥1 dose of JZP-110, and were included in the safety population (FIG. 2). 17 of 174 patients (10%) discontinued in the Titration Phase. 9 of 157 patients (7%) discontinued in the Stable-Dose Phase. An additional 21 patients (14%) did not meet the improvement criteria for randomization. Four patients who were randomized were not included in the mITT population. Table 1 shows the baseline demographic and clinical characteristics of the safety population.

Baseline demographics are representative of the clinical OSA population with mean age in the mid-50-year range, predominantly male, and BMI >30 (Table 1). Patients had ES at baseline, indicated by mean ESS scores >15, and mean MWT sleep latencies of 15-16 minutes. Baseline demographic and clinical characteristics were similar among treatment groups across study phases.

Figures 3A, 3B:
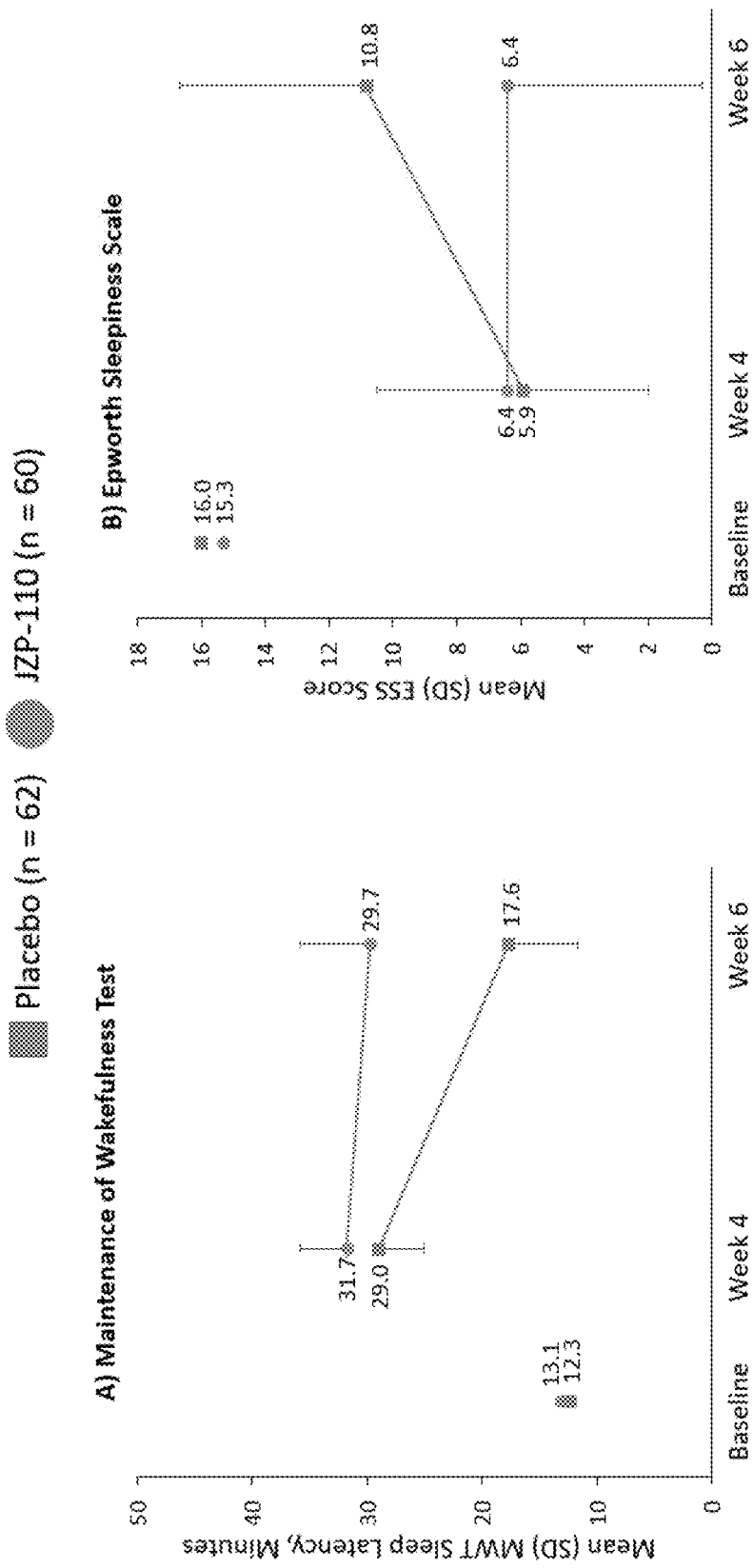
FIGS. 3A-3B show MWT and ESS values (co-primary endpoints) for patients who entered the double-blind withdrawal phase. Values are modified intent-to-treat population (n=122). ESS, Epworth Sleepiness Scale; MWT, Maintenance of Wakefulness Test.

Baseline values in the mITT population (FIGS. 3A and 3B) were similar to those in the safety population (Table 1). After 4 weeks of APC treatment, MWT mean sleep latency increased from 12.3 to 29.0 minutes and from 13.1 to 31.7 minutes (FIG. 3A), and ESS scores decreased from 16.0 to 5.9 and from 15.3 to 6.4 (FIG. 3B) in the randomized patients. During the Double-Blind Withdrawal Phase (from week 4 to week 6), patients who had improved on APC, and who continued to receive JZP-110, remained improved on the MWT and ESS, whereas patients who were switched to placebo worsened on both measures (FIGS. 3A and 3B). A breakdown of the results by the level of increase is shown in Table 2.

Figures 4A, 4B:
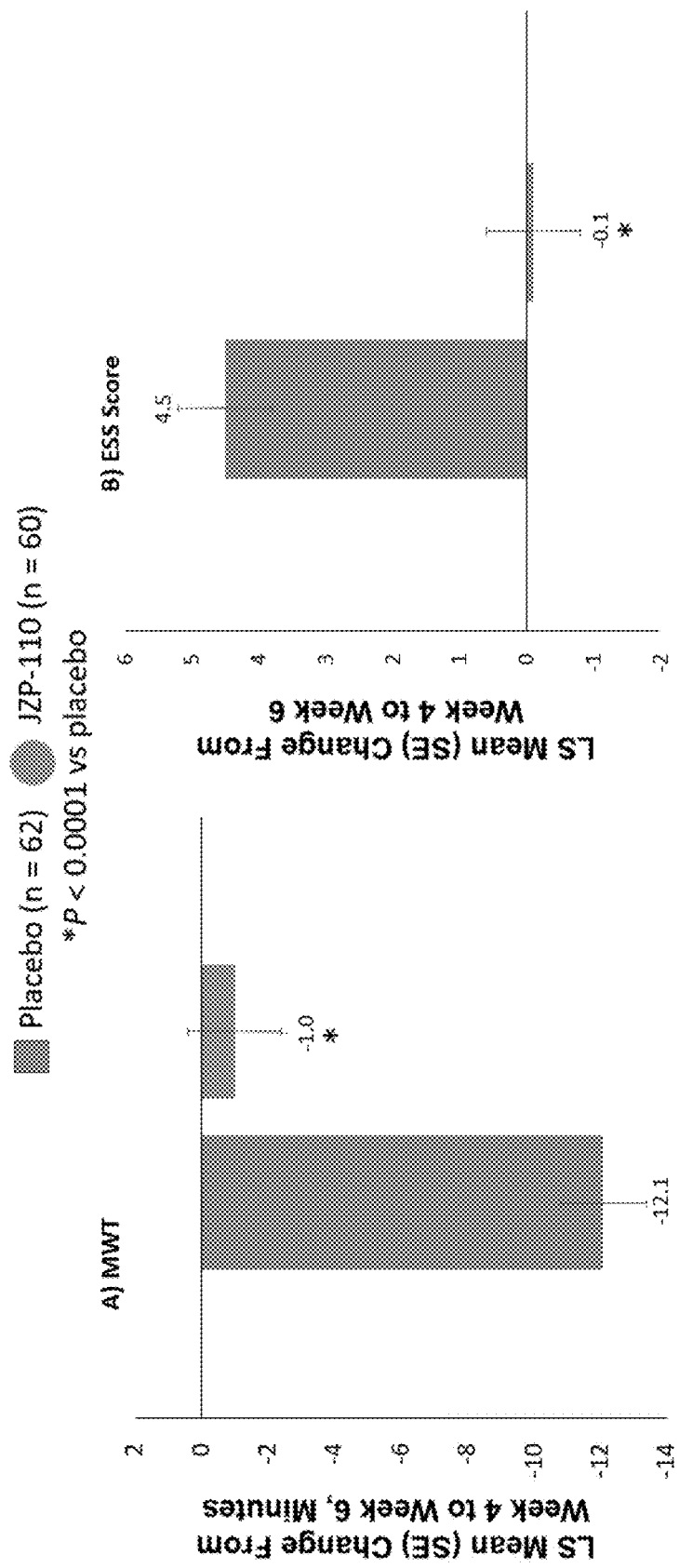
FIGS. 4A-4B show the change From week 4 to 6 on the MWT and ESS values (co-primary endpoints) in the double-blind Withdrawal Phase. Values are modified intent-to-treat population (n=122). *P<0.0001 vs. placebo. ESS, Epworth Sleepiness Scale; LS, least squares, MWT, Maintenance of Wakefulness Test.

Mean MWT sleep latency decreased by 12.1 minutes from week 4 to week 6 in patients who were switched to placebo during the Double-Blind Withdrawal Phase compared with a change of −1.0 minute for those who remained on JZP-110 (P<0.0001; FIG. 4A). Mean ESS score increased by 4.5 among patients who were switched to placebo during the Double-Blind Withdrawal Phase compared with a mean decrease of 0.1 for those who stayed on APC (P<0.0001; FIG. 4B).

Figure 5:
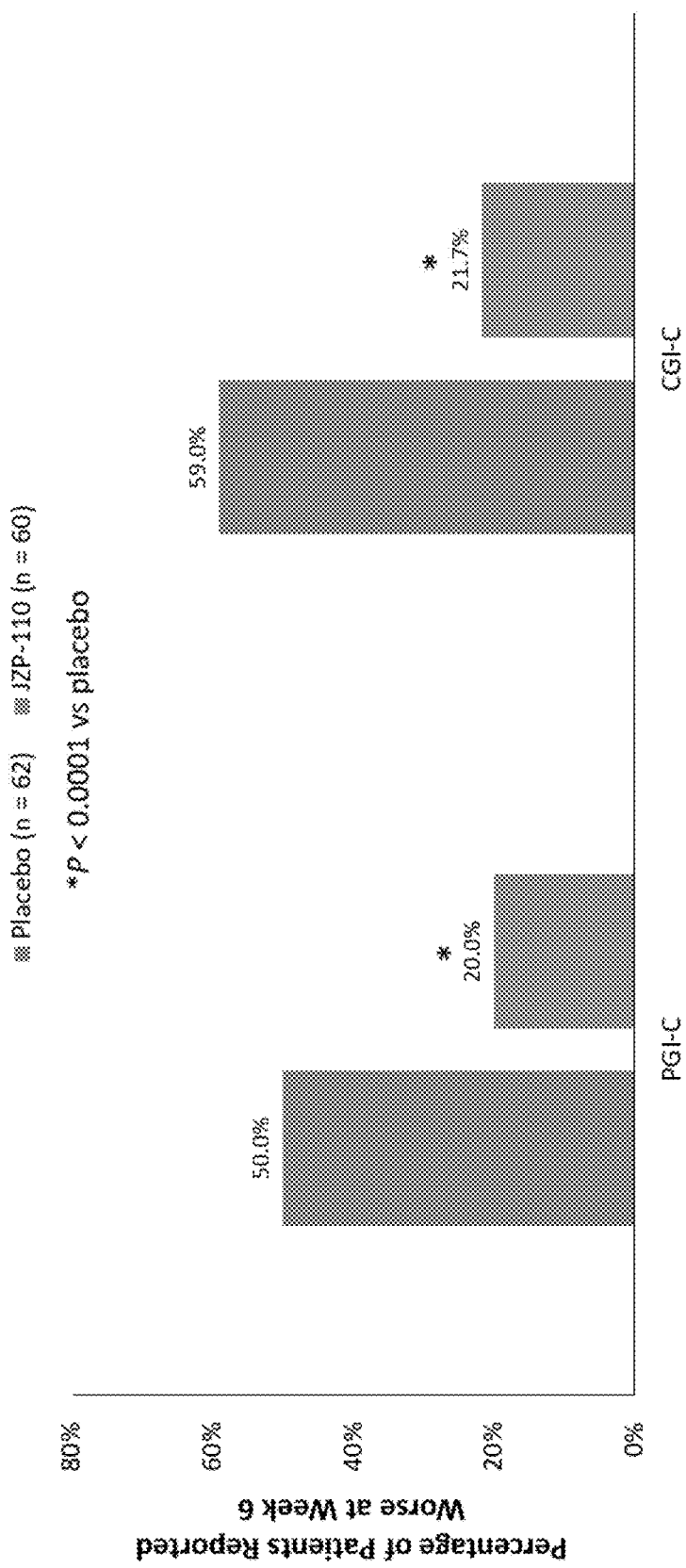
FIG. 5 shows the percentage of patients who had an overall worsening of their condition in the double-blind Withdrawal Phase. *P<0.0001 vs. placebo. Values are modified intent-to-treat population. CGI-C, Clinician Global Impression of Change; PGI-C, Patient Global Impression of Change.

Significantly higher percentages of patients who were switched to placebo experienced a worsening of their overall condition on the PGI-C and CGI-C as compared with patients who stayed on APC (FIG. 5).

More TEAEs occurred during the Titration Phase (48.9%) rather than during the Stable-Dose Phase (10.2%) (Table 3). The most common TEAEs during the Titration Phase were headache, dry mouth, nausea, dizziness, insomnia, palpitations, and anxiety. The Randomized Withdrawal Phase had few TEAEs (Table 4). There was no evidence of rebound hypersomnia or withdrawal effects after abrupt discontinuation of APC in the placebo group in the Randomized Withdrawal Phase. There were no serious TEAEs in the study.

In conclusion the study showed that patients who completed the 4-week treatment and remained on APC did not show loss of efficacy relative to those who were randomized to treatment withdrawal. No rebound sleepiness or discontinuation-related adverse events were observed after APC withdrawal.

These results support APC efficacy for treatment of ES in adults with OSA. Safety and tolerability of APC were consistent with earlier phase 2 studies for the treatment of narcolepsy (Bogan et al., *Sleep Med.* 16(9):1102 (2015); Ruoff et al., *Sleep* 39(7):1379 (2016)). TEAEs were primarily reported during the initial Titration Phase. The most frequently reported TEAEs (≥5%) during the Titration Phase were headache, dry mouth, nausea, dizziness, insomnia with fewer of these during the Stable-Dose Phase, and none during the Withdrawal Phase.

Example 2

Function and Work Productivity Measures in a Phase 3 Study of the Safety and Efficacy of APC for the Treatment of Excessive Sleepiness in Subjects with Obstructive Sleep Apnea Excessive sleepiness (ES), one of the main presenting symptoms of patients with obstructive sleep apnea (OSA), is associated with work disability and impaired productivity (Nena et al., *J. Occup. Environ. Med.* 52(6):622 (2010); Omachi et al., *Sleep* 32(6):791 (2009); Mulgrew et al., *Sleep Med.* 9(1):42 (2007); Hirsch Allen et al., *Chest* 147(5):1422 (2015)). APC is a selective dopamine norepinephrine reuptake inhibitor with wake-promoting effects that is being evaluated for the treatment of ES in patients with OSA, narcolepsy, and Parkinson disease.

The objective of this study was to evaluate the effects of APC hydrochloride on daytime functioning, work productivity, and activity impairment in adult patients with OSA and ES.

The study was a 12-week, double-blind, placebo-controlled, parallel design study as described in greater detail in Example 1 (Schweitzer et al., *Sleep* 40(*Abstract Supplement*):A237. Abstract 0641 (2017)). Patients were randomized (1:1:2:2:2) to APC 37.5, 75, 150, 300 mg, or placebo for 12 weeks, and were stratified by adherence or nonadherence with primary OSA therapy (adherent definition was use for ≥4 hours per night on >70% of nights). Two patient-reported measures were included as secondary efficacy outcomes to evaluate the effects of APC on functional status and work productivity and activity impairment at baseline and weeks 1, 4, 8, and 12. The Functional Outcomes of Sleep questionnaire short version (FOSQ-10) (Chasens et al., *Sleep* 32(7):915 (2009)) evaluated the effects of ES on functioning. The Work Productivity and Activity Impairment questionnaire for Specific Health Problems (WPAI:SHP) (Reilly et al., *Pharmacoeconomics* 4(5):353 (1993); Reilly, Work Productivity and Activity Impairment Questionnaire: Specific Health Problem V2.0 (WPAI:SHP). www.reillyassociates.net/WPAI_SHP) evaluated work productivity impairment among employed patients and overall activity impairment outside of work among all patients for the past 7 days. Four outcomes are available from the WPAI:SHP: Absenteeism (percent work time missed due to health); Presenteeism (percent impairment while working due to health); Percent overall work impairment (calculated from absenteeism and presenteeism); and Percent activity impairment due to health. The FOSQ-10 was evaluated as change over time compared with placebo (least squares (LS) mean); the 4 WPAI outcomes were evaluated at week 12 compared to placebo. Efficacy analyses were based on the modified intent-to-treat population (mITT) and there was no multiplicity adjustment for the FOSQ-10 or WPAI:SHP. Safety and tolerability were assessed based on treatment-emergent adverse events (TEAEs), vital signs, electrocardiogram test, physical exams, Columbia-Suicide Severity Rating Scale, and laboratory tests in the safety population.

Baseline characteristics were similar among the treatment groups. The safety population (n=474) was primarily male, white, and were about mid-50 years old (Table 5). Patients had moderate ES as indicated by ESS scores (range, 14.8-15.6) and short MWT sleep latency times (range, 12.0-13.6 minutes). The majority of patients were rated by the clinicians as being moderately or markedly ill. The mITT population consisted of 459 patients, of whom 404 (88.0%) completed the study. Adverse events were the primary reason for withdrawal and none discontinued due to lack of efficacy. Co-primary MWT and ESS endpoints were met at all doses (Table 6). The key secondary endpoint based on Patient Global Impression of Change (PGI-C) was met for all doses except APC 37.5 mg (Table 6).

Figure 6:
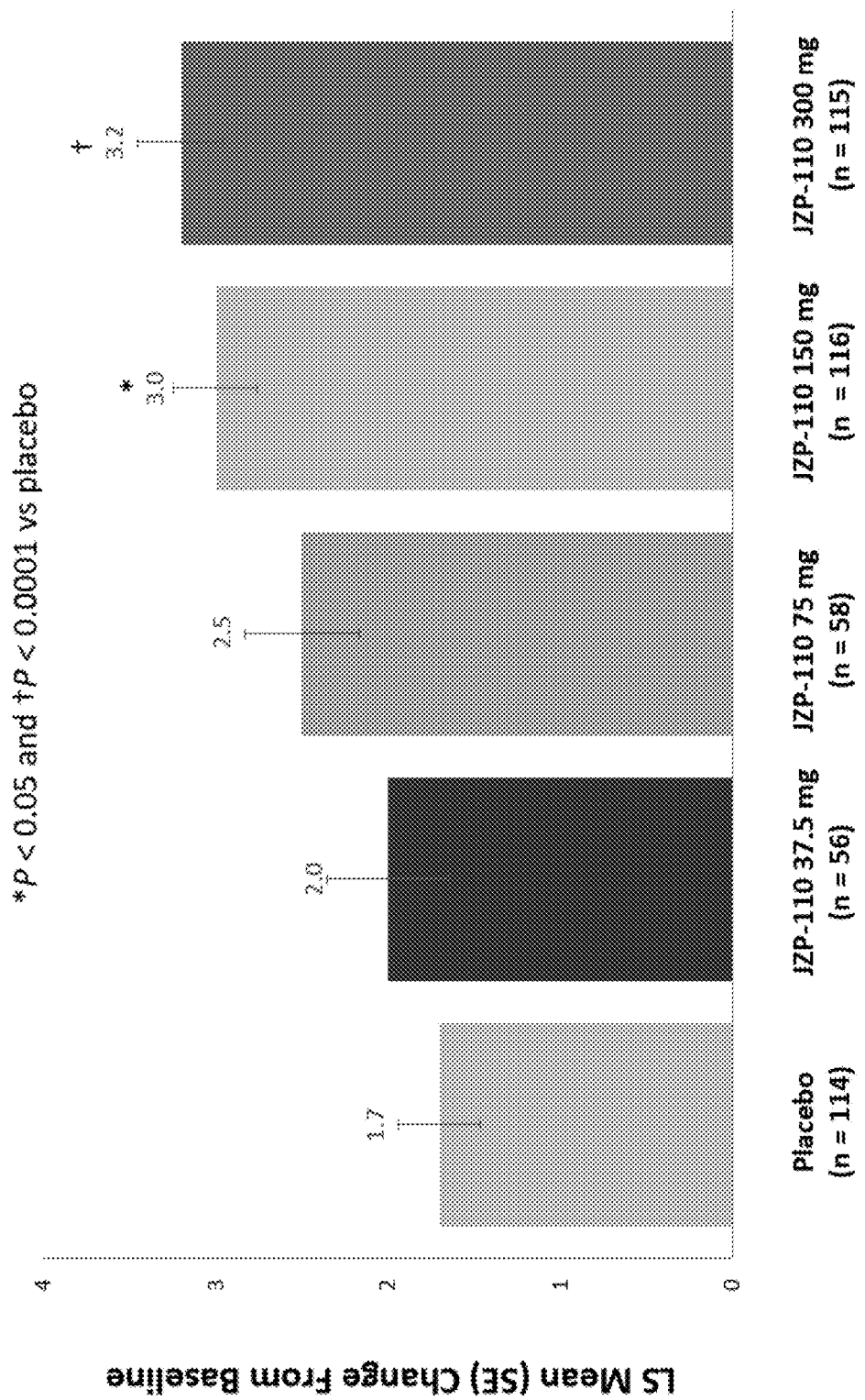
FIG. 6 shows the change from baseline to week 12 in FOSQ-10 total score. Values are for the modified intent-to-treat population (n=459). FOSQ-10, Functional Outcomes of Sleep questionnaire short version; LS, least squares; SE, standard error.

APC dose dependently increased FOSQ-10 scores at week 12 with statistically significant effects at the 150 and 300 mg doses relative to placebo (FIG. 6). Improvements were observed as early as week 1 for the 150 and 300 mg doses.

Figure 7:
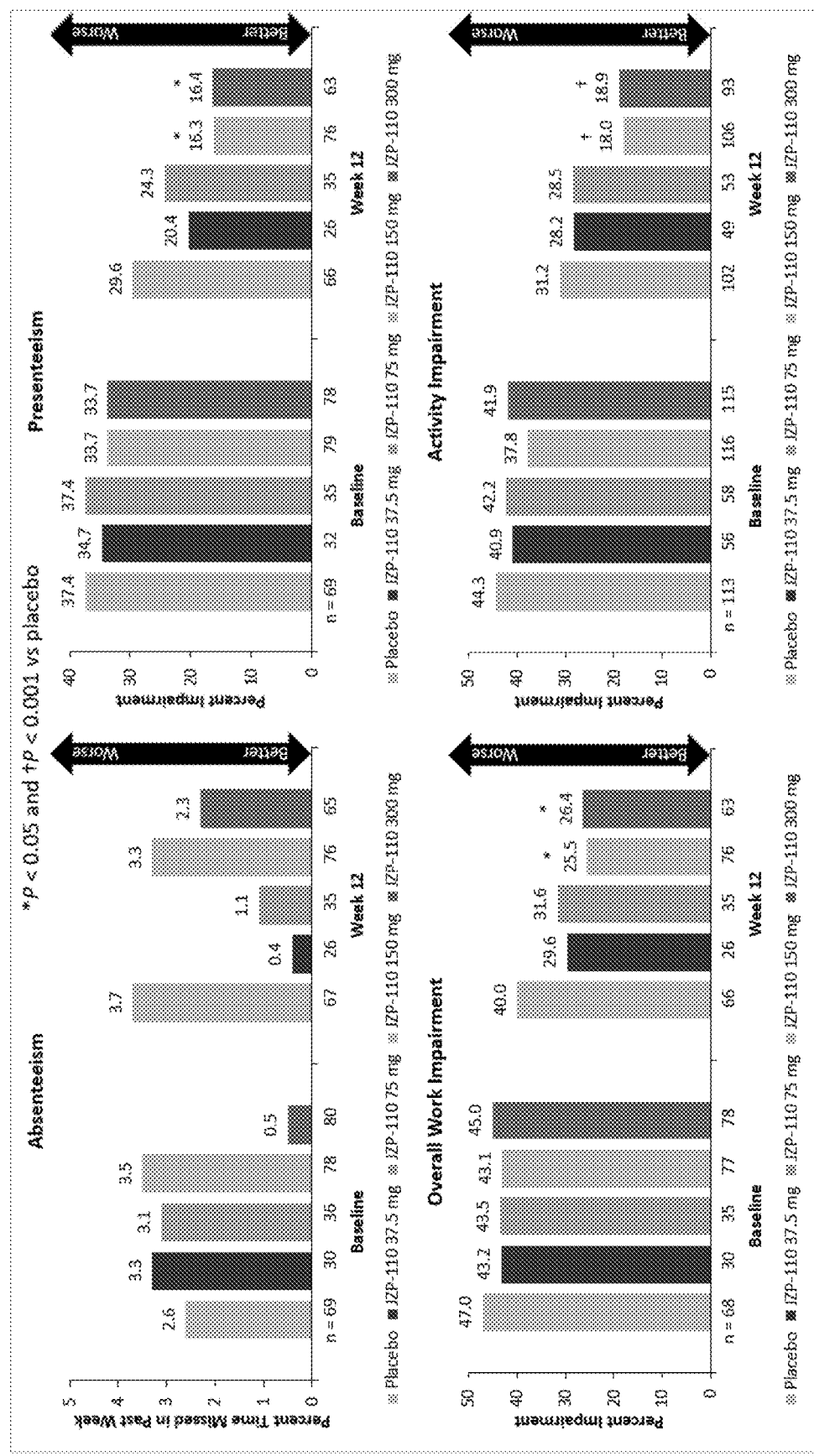
FIG. 7 shows the percentage of lost productivity and activity impairment in the past week as measured by the WPAI:SHP, with OSA specified as the health problem. Values are for the modified intent-to-treat population (n=459). Absenteeism, presenteeism, and overall work impairment evaluated along in employed subjects (N=). OSA, obstructive sleep apnea; WPAI:SHP, Work Productivity and Activity Impairment questionnaire for Specific Health Problems.

Among the 224 (48.8%) patients who were employed, OSA had a substantial impact on their self-reported work and activity impairment (FIG. 7). Presenteeism (impaired productivity while at work) appeared to be the main driver of overall work impairment among patients who were employed. Absenteeism was relatively low, with patients missing from 0.5% to 3.5% of work per week at baseline. Activity impairment outside of work ranged from 37.8% to 44.3% at baseline. At week 12, APC, at doses of 150 and 300 mg, had significantly decreased lower presenteeism, overall work impairment, and activity impairment (outside of work) compared to placebo.

The most common TEAEs were headache, nausea, decreased appetite, anxiety, nasopharyngitis, and insomnia (Table 7). The incidence of TEAEs and discontinuation due to TEAEs generally appeared to be dose dependent (Table 7). Seven serious TEAEs were reported in 5 patients: goiter (n=1) and back pain/sciatica resulting from a motor vehicle accident (n=1) in placebo; bile duct obstruction (n=1) and streptococcal endocarditis (n=1) in JZP-110 37.5 mg; and hyperglycemia (n=1) in JZP-110 150 mg. There was 1 non-treatment-emergent serious adverse event of coronary artery disease, which began prior to the patient receiving JZP-110 300 mg, of moderate severity; a coronary stent was inserted and the patient recovered. APC had a modest effect on blood pressure and pulse rate. There was a mean increase from baseline of 1-4 mmHg in systolic blood pressure and 1-3 mmHg in diastolic blood pressure and a mean increase from baseline of 2-5 beats/minute in pulse rate.

In conclusion, APC met the co-primary MWT and ESS endpoints at all doses and the key secondary PGI-C endpoint at all doses except 37.5 mg. APC 150 and 300 mg resulted in dose-dependent and statistically significant improvements in patient-reported functioning and activities on the FOSQ-10. APC 150 and 300 mg had significantly lower presenteeism and overall work impairment on the WPAI:SHP at week 12 compared with placebo. APC had significantly less activity impairment compared with placebo at week 12, defined as the ability to do their regular daily activities (other than work at a job). Safety and tolerability were consistent with previous phase 2 studies of APC in patients with narcolepsy (Bogan et al., *Sleep Med.* 16(9):1102 (2015); Ruoff et al., *Sleep* 39(7):1379 (2016)). The most frequently reported TEAEs (≥5% in any group) were headache, nausea, decreased appetite, anxiety, nasopharyngitis, and insomnia.

Example 3

SF-36 and EQ-5D-5L Measures in a Phase 3 Study of the Safety and Efficacy of APC for the Treatment of Excessive Sleepiness in Subjects with Obstructive Sleep Apnea Excessive sleepiness (ES) is a frequent symptom of obstructive sleep apnea (OSA) that persists in up to 62.5% of patients despite primary OSA therapy (Weaver et al., *Sleep* 30(6):711 (2007)). ES adversely impacts specific domains of health-related quality-of-life (HRQoL) in patients with OSA. Studies using the 36-item Short Form Health Survey (SF-36) have shown that Vitality and Role Physical were particularly affected (Smith el al., *J. Sleep Res.* 4(3):183 (1995); Jenkinson et al., *J. Sleep Res.* 6(3): 199 (1997); Bennett et al., *Am. J. Respir. Crit. Care Med.* 159(6):1884 (1999); Sin et al., *Chest* 122(5):1679 (2002)). APC is a selective dopamine norepinephrine reuptake inhibitor with wake-promoting effects that is being evaluated for the treatment of ES in patients with OSA, narcolepsy, and Parkinson disease.

This study evaluated the effects of APC on patient-reported HRQoL in adult patients with OSA and ES using the SF-36 version 2 (SF-36 v2)[7] and the 5-dimension, 5-level EuroQol (EQ-5D-5L) (The EuroQol Group. *EQ-5D-5L User Guide*. Version 2.1. April 2015. www.euroqol.org/fileadmin/user_upload/Documenten/PDF/Folders_Flyers/EQ-5D-5L_UserGuide_2015.pdf).

This was a 12-week, double-blind, placebo-controlled, parallel-design study. Patients were randomized (1:1:2:2:2) to APC 37.5 mg, 75 mg, 150 mg, or 300 mg, or placebo for 12 weeks, and were stratified by adherence or nonadherence with primary OSA therapy.

The SF-36 v2 consists of 2 summary scales (Physical Component Summary and Mental Component Summary) and 8 specific health status domains (Physical Function, Role Physical, Bodily Pain, General Health, Vitality, Social Functioning, Role Emotional, Mental Health) (Ware Jr et al., *User's Manual for the SF-36v2™ Health Survey* (2nd ed.). QualityMetric Incorporated (Lincoln, R.I.); 2007). The EQ-5D-5L consists of 5 questions/dimensions (Mobility, Self-care, Usual Activities, Pain/Discomfort, and Anxiety/Depression) that have 5 response levels each (no problems, slight problems, moderate problems, severe problems, and extreme problems/unable to do) that are used to derive an overall EQ-5D-5L index score (0=death, 1=perfect health), and a health status visual analog scale (VAS) that is anchored at 0 with "the worst health you can imagine" and at 100 with "the best health you can imagine." (The EuroQol Group. *EQ-5D-5L User Guide*. Version 2.1. April 2015. www.euroqol.org/fileadmin/user_upload/Documenten/PDF/Folders_Flyers/EQ-5D-5L_UserGuide_2015.pdf)

Efficacy analyses were based on the modified intent-to-treat (mITT) population; there was no multiplicity adjustment for the SF-36 v2 or EQ-5D-5L. SF-36 v2 scores were scaled from 0 to 100 (higher scores on all scales represent better health), transformed to norm-based scores using US general-population data from SF-36 Manuals (Ware Jr et al., *User's Manual for the SF-36v2™ Health Survey* (2nd ed.). QualityMetric Incorporated (Lincoln, R.I.); 2007), and were analyzed using a mixed-effect model with repeated measures (MMRM); and baseline value of the efficacy endpoint was used to determine differences in changes from baseline. EQ-5D-5L VAS and index-score data were analyzed using an MMRM model. Safety and tolerability were assessed based on treatment-emergent adverse events (TEAEs), vital signs, electrocardiogram test, physical exams, and laboratory tests.

Baseline characteristics were similar among the treatment groups. The safety population (n=474) was primarily male (62.7%), white (76.2%), and had a mean (standard deviation [SD]) age of 53.9 (10.9) years (Table 8). Patients had moderate ES as indicated by ESS scores (range, 14.8-15.6) and short MWT sleep latency times (range, 12.0-13.6 minutes). The majority of patients (75.3%) were rated by the clinicians as being moderately or markedly ill. The mITT population consisted of 459 patients, of whom 404 (88.0%) completed the study. The main reason for discontinuation was adverse events and no patients discontinued due to lack of efficacy.

Complete primary results are presented in Example 1. Coprimary endpoints (change from baseline to week 12 in MWT and ESS) were met at all doses (Table 9). A key secondary endpoint, Patient Global Impression of Change (PGI-C), was met at all doses except for APC 37.5 mg (Table 9).

Figure 8:
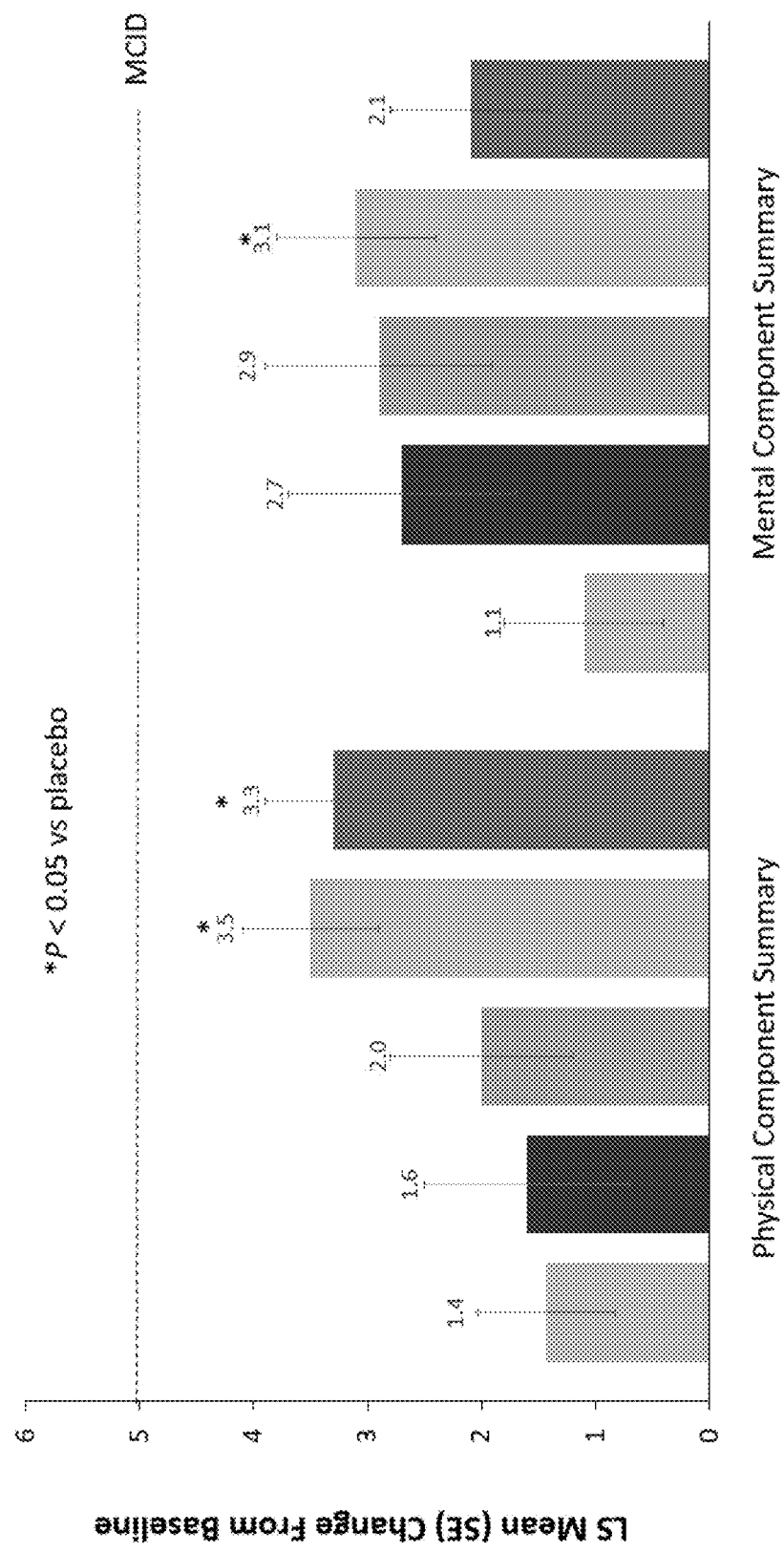
FIG. 8 shows the change from baseline at week 12 on the physical and mental component summary scores of the SF-36v2. Values are for the modified intent-to-treat population (n=459). Dashed horizontal line represents the MCID for a change in SF-36v2 score.[10] *P<0.05. LS, least squares.

Dose-dependent increases in the Physical Component Summary Scale were statistically significant at APC 150, and 300 mg (FIG. 8). Mental Component Summary scores were similar at APC 37.5, 75, and 150 mg with only APC 150 mg reaching statistical significance (FIG. 8). The changes on the Physical Component Summary and Mental Component Summary did not exceed the minimal clinically important difference (MCID).

Among the individual SF-36 domains, the largest effects of APC were observed on Vitality followed by Role Physical (FIG. 9). These 2 domains showed the greatest impairment at baseline as indicated by having the lowest scores across all treatment groups. On the Vitality domain, there appeared to be a dose-dependent response that exceeded the MCID at APC 75, 150, and 300 mg (FIG. 9), with statistically significant improvements relative to placebo at APC 150 and 300 mg. APC 150 mg also resulted in significantly greater changes from baseline relative to placebo on Role Physical, General Health, Social Functioning, and Role Emotional (FIG. 9).

Effects of APC on the EQ-5D VAS appeared to be dose dependent, but were not significantly different from placebo (FIG. 10A). There were no significant effects on the EQ-5D-5L index value (FIG. 10B).

The most common TEAEs were headache, nausea, decreased appetite, anxiety, nasopharyngitis, and insomnia (Table 10). The incidence of TEAEs and discontinuation due to TEAEs generally appeared to be dose dependent. It is possible that the lower incidence of TEAEs in the APC 150 mg relative to the 300 mg may account, at least in part, for the greater improvements in HRQoL relative to the higher dose. Seven serious TEAEs were reported in 5 patients: goiter (n=1) and back pain/sciatica resulting from a road accident (n=1) in placebo; bile duct obstruction (n=1), and streptococcal endocarditis (n=1) in APC 37.5 mg; and hyperglycemia (n=1) in JZP-110 150 mg. There was 1 non-treatment-emergent serious adverse event of coronary artery disease, which began prior to the patient receiving APC 300 mg, of moderate severity; a coronary stent was inserted and the patient recovered. APC had a modest effect on blood pressure and pulse rate, with a mean increase from baseline of 1-4 mmHg in systolic blood pressure and 1-3 mmHg in diastolic blood pressure and mean increase from baseline of 2-5 beats/minute in pulse rate.

In conclusion, APC met the primary efficacy endpoints of reducing ES at all doses except 37.5 mg. The most common TEAEs were headache, nausea, decreased appetite, anxiety, nasopharyngitis, and insomnia and generally consistent with safety profile of APC in N and OSA. Treatment with APC was associated with improvements in HRQoL as measured on the SF-36v2. APC 150 mg had the greatest impact on the SF-36v2 subscales with statistically significant improvements on the Physical and Mental Component Summary Scales, and on the Role Physical, General Health, Vitality, Social Functioning, and Role Emotional domains. APC 300 mg showed significantly greater improvements relative to placebo on Role Physical and Vitality domains and on the Physical Component Summary Scale. The Vitality domain for JZP-110 75, 150, and 300 mg exceeded the MCID threshold. No significant changes were observed on the EQ-5D-5L index or VAS scores, suggesting that this measure does not capture dimensions of relevance to OSA (e.g., mobility, self-care, pain). Baseline scores on the SF-36v2 and the EQ-5D-5L were close to population norms and did not indicate marked impairment at baseline even though these patients had substantial ES as manifested by their baseline MWT sleep latency times and ESS scores.

Example 4

Phase 3 Study of APC in Subjects with Narcolepsy

Narcolepsy is a chronic neurological disorder that results from the dysregulation of neurophysiologic pathways that control the stability of sleep and wake states (Dauvilliers et al., Lancet 369(9560):499 (2007)). Excessive sleepiness (ES) is a debilitating symptom that is present in all patients with narcolepsy (American Academy of Sleep Medicine. *The International Classification of Sleep Disorders—Third Edition* (ICSD-3). Darien, Ill.: American Academy of Sleep Medicine; 2014). APC is a selective dopamine and norepinephrine reuptake inhibitor with robust wake-promoting effects as demonstrated in rodent models of narcolepsy and in two phase 2 clinical trials in adult patients with narcolepsy (Bogan et al., Sleep Med. 16(9):1102 (2015); Ruoff et al., Sleep 39(7):1379 (2016)).

The object of the study was to evaluate the efficacy and safety of APC hydrochloride (JZP-110) for the treatment of ES and impaired wakefulness in patients with narcolepsy type 1 or type 2 (formerly narcolepsy with and without cataplexy, respectively).

The study was a 12-week, double-blind, randomized, placebo-controlled, parallel-group study. Patients were randomized (1:1:1:1) to receive placebo or APC 75, 150, or 300 mg; randomization was stratified by the presence or absence of cataplexy.

Key inclusion criteria included adults 18-75 years old, inclusive, with a diagnosis of narcolepsy type 1 or type 2 according to ICSD-3 (American Academy of Sleep Medicine. *The International Classification of Sleep Disorders—Third Edition* (ICSD-3). Darien, Ill.: American Academy of Sleep Medicine; 2014) or DSM-5 (American Psychiatric Association. *Diagnostic and Statistical Manual of Mental Disorders Fifth Edition* (DSM-5). Arlington, Va.: American Psychiatric Association; 2013) criteria, baseline mean sleep latency <25 minutes on the first 4 trials of a 5-trial, 40-minute Maintenance of Wakefulness Test (MWT) and baseline Epworth Sleepiness Scale (ESS) (Johns, Sleep 14(6):540 (1991)) score ≥10, usual nightly total sleep time ≥6 hours, and body mass index between 18 and 45 kg/m².

Key exclusion criteria include any medical conditions other than narcolepsy, behaviors such as night-time or variable shift work, or use of medications that could affect the evaluation of ES or cataplexy and history or presence of any acutely unstable medical condition, behavioral or psychiatric disorder, or surgical history that could affect the safety of the participant.

Co-primary endpoints were change from baseline to week 12 in MWT mean sleep latency and ESS score. The key secondary endpoint was the percentage of patients who reported improvement on the Patient Global Impression of Change (PGI-C) (Guy, *ECDEU assessment manual for psychopharmacology, revised. US Department of Health, Education, and Welfare publication* (ADM 76-338). Rockville, Md.: National Institute of Mental Health; 1976) at week 12. Other secondary and exploratory endpoints included changes on function and quality-of-life and changes in the number of cataplexy attacks per week. Safety evaluation included adverse events, laboratory tests, and vital signs.

Efficacy analyses were based on the modified intent-to-treat population (mITT), defined as all patients who were randomized, received at least 1 dose of study drug, and had baseline and at least 1 post-baseline evaluation of both MWT and ESS. MWT and ESS were analyzed using a mixed-effect repeated measures (MMRM) model. PGI-C was analyzed using a chi-square test. A fixed hierarchical testing procedure was used to correct for multiplicity, starting with the highest dose of APC for the co-primary endpoints and the key secondary endpoint; testing proceeded with each subsequent lower doses.

Of the 239 patients who were randomized, 236 received at least 1 dose of study drug and were included in the safety population (FIG. 11). The discontinuation rate was highest in JZP-110 300 mg (27.1%) compared with placebo (11.9%), JZP-110 75 mg (16.9%), and JZP-100 150 mg (13.6%) (FIG. 11). The most common reasons for discontinuation in APC 300 mg were lack of efficacy (10.2%; n=6) and adverse events (8.5%; n=5). The mITT population consisted of 231 patients. 1 patient randomized to placebo and 4 patients randomized to JZP-110 150 mg did not have baseline or at least one post-baseline efficacy assessments of MWT and ESS.

The patient population was 64.9% female, 79.7% white, with a mean (standard deviation) age of 36.2 (13.2) years. The majority of patients (64.5%) were rated by clinicians as moderately or markedly ill and had mean baseline MWT sleep latency of 6.2-8.7 minutes and mean ESS scores of 17.0-17.3. Demographic and clinical characteristics were similar across treatment groups in the mITT population (Table 11).

The study met the co-primary endpoints of change from baseline in MWT and ESS, and the key secondary endpoint of percentage of patients with PGI-C improvement at JZP-110 150 and 300 mg (Table 12).

APC significantly increased MWT mean sleep latency relative to placebo at 150 and 300 mg at week 12 (FIG. 12; mITT population). Statistically significant effects were observed at all doses as early as week 1. Effects on the MWT were dose dependent and stable over the 12 weeks of the study. A breakdown of the results by the level of increase is shown in Table 13.

APC significantly decreased ESS scores relative to placebo at all doses at week 12 (FIG. 13; mIT population). Statistically significant effects were observed at APC 150 and 300 mg as early as week 1. Effects on the ESS were dose dependent and stable over the 12 weeks of the study.

APC significantly increased the percentage of patients who reported improvement in their overall condition at all doses (nominal P-value at 75 mg) relative to placebo at week 12 (FIG. 14; mITT population). Statistically significant effects were observed at all doses as early as week 1. Patient-rated improvement was dose dependent and stable over the 12 weeks of the study.

The most common TEAEs (≥5%) in all JZP-110 groups were headache, nausea, decreased appetite, nasopharyngitis, dry mouth, and anxiety (Table 14). In general, the incidence of the most common TEAEs was dose dependent. One patient in APC 150 mg group had 2 serious TEAEs of non-cardiac chest pain and anxiety that were deemed to be not related by the investigator; this patient continued in the study. Discontinuations due to TEAEs were greater than placebo in the APC 150 and 300 mg groups.

In conclusion, APC 150 and 300 mg resulted in statistically significant and robust effects at week 12 on the MWT, ESS, and PGI-C, which is consistent with findings from previous phase 2 studies in patients with narcolepsy.[3,4] At 75 mg, significant effects were observed on the ESS but not on the MWT. Efficacy was dose related for all co-primary and key secondary endpoints. Effects were observed as early as week 1 and were maintained over the 12 weeks of the study, demonstrating that there was no apparent tolerance to the wake-promoting effects of APC over the 12 weeks of the study. Safety and tolerability were consistent with the previous phase 2 studies in patients with narcolepsy (Bogan et al., *Sleep Med.* 16(9):1102 (2015); Ruoff et al., *Sleep* 39(7): 1379 (2016)). Common TEAEs (≥5%) were headache, nausea, decreased appetite, nasopharyngitis, dry mouth, and anxiety.

The foregoing is illustrative of the present invention, and is not to be construed as limiting thereof. The invention is defined by the following claims, with equivalents of the claims to be included therein. All publications, patent applications, patents, patent publications, and any other references cited herein are incorporated by reference in their entireties for the teachings relevant to the sentence and/or paragraph in which the reference is presented.

TABLE 1

Baseline Demographic and Clinical Characteristics of the Safety Population

| Variable | Titration Phase, All JZP-110 Doses (n = 174) | Stable-Dose Phase, All JZP-110 Doses (n = 157) | Double-Blind Withdrawal Phase | |
| --- | --- | --- | --- | --- |
| | | | Placebo (n = 62) | All JZP-110 Doses (n = 62) |
| Baseline Characteristics | | | | |
| Age, years, mean (SD) | 54.8 (10.5) | 55.4 (10.2) | 56.2 (9.8) | 56.3 (11.4) |
| Sex, n (%) | | | | |
| Male | 107 (61.5) | 97 (61.8) | 41 (66.1) | 36 (58.1) |
| Female | 67 (38.5) | 60 (38.2) | 21 (33.9) | 26 (41.9) |
| Race | | | | |
| White | 137 (78.7) | 121 (77.1) | 45 (72.6) | 50 (80.6) |
| Black or African American | 34 (19.5) | 34 (21.7) | 15 (24.2) | 12 (19.4) |
| Other | 3 (1.7) | 2 (1.3) | 2 (3.2) | 0 |
| BMI, kg/m$^2$, mean (SD) | 33.3 (5.4) | 33.3 (5.2) | 33.3 (5.5) | 32.9 (5.0) |
| Baseline Clinical Characteristics | | | | |
| MWT, minutes, mean (SD) | 13.2 (7.5) | 12.9 (7.1) | 12.3 (7.9) | 13.0 (6.7) |
| ESS, mean (SD) | 15.4 (3.4) | 15.5 (3.5) | 16.0 (3.5) | 15.3 (3.5) |
| CGI-S, n (%) | | | | |
| 1 = Normal | 0 | 0 | 0 | 0 |
| 2 = Borderline ill | 6 (3.4) | 6 (3.8) | 3 (4.8) | 2 (3.2) |
| 3 = Mildly ill | 21 (12.1) | 18 (11.5) | 7 (11.3) | 6 (9.7) |
| 4 = Moderately ill | 71 (40.8) | 61 (38.9) | 23 (37.1) | 23 (37.1) |
| 5 = Markedly ill | 43 (24.7) | 41 (26.1) | 15 (24.2) | 20 (32.3) |
| 6 = Severely ill | 28 (16.1) | 26 (16.6) | 11 (17.7) | 10 (16.1) |
| 7 = Among the most extremely ill patients | 5 (2.9) | 5 (3.2) | 3 (4.8) | 1 (1.6) |

BMI, body mass index; CGI-S, Clinical Global Impression of Severity; ESS, Epworth Sleepiness Scale; MWT, Maintenance of Wakefulness Test.

TABLE 2

MWT Mean Sleep Latency (minutes): Summary of Change from Baseline Categories by Visit (mITT Population)

| Parameter Visit | Placebo N = 114 | 37.5 mg N = 56 | 75 mg N = 58 | 150 mg N = 116 | 300 mg N = 115 | Combined JZP-110 N = 345 |
|---|---|---|---|---|---|---|
| *Increase from Baseline* | | | | | | |
| *Week 1* | | | | | | |
| n | 35 | 18 | 17 | 33 | 37 | 105 |
| >=5 minutes, (%) | 11 (31.4) | 4 (22.2) | 11 (64.7) | 27 (81.8) | 28 (75.7) | 70 (66.7) |
| >=10 minutes, (%) | 4 (11.4) | 2 (11.1) | 6 (35.3) | 22 (66.7) | 22 (59.5) | 52 (49.5) |
| >=15 minutes, (%) | 2 (5.7) | 2 (11.1) | 4 (23.5) | 13 (39.4) | 19 (51.4) | 38 (36.2) |
| >=20 minutes, (%) | 1 (2.0) | 2 (11.1) | 1 (5.9) | 9 (27.3) | 14 (37.8) | 26 (24.8) |
| >=25 minutes, (%) | 0 | 0 | 1 (5.9) | 4 (12.1) | 7 (18.9) | 12 (11.4) |
| >=30 minutes, (%) | 0 | 0 | 0 | 2 (6.1) | 4 (10.8) | 6 (5.7) |
| *Week 4* | | | | | | |
| n | 107 | 50 | 55 | 108 | 101 | 314 |
| >=5 minutes, (%) | 29 (27.1) | 21 (42.0) | 34 (61.8) | 83 (76.9) | 79 (78.2) | 217 (69.1) |
| >=10 minutes, (%) | 18 (16.8) | 16 (32.0) | 25 (45.5) | 54 (50.0) | 63 (62.4) | 158 (50.3) |
| >=15 minutes, (%) | 10 (9.3) | 7 (14.0) | 11 (20.0) | 40 (37.0) | 47 (46.5) | 105 (33.4) |
| >=20 minutes, (%) | 4 (3.7) | 4 (8.0) | 5 (9.1) | 26 (24.1) | 32 (31.7) | 67 (21.3) |
| >=25 minutes, (%) | 2 (1.9) | 0 | 2 (3.6) | 13 (12.0) | 15 (14.9) | 30 (9.6) |
| >=30 minutes, (%) | 2 (1.9) | 0 | 1 (1.8) | 3 (2.8) | 5 (5.0) | 9 (2.9) |
| *Week 12* | | | | | | |
| n | 99 | 49 | 54 | 105 | 92 | 300 |
| >=5 minutes, (%) | 22 (22.2) | 18 (36.7) | 35 (64.8) | 71 (67.6) | 69 (75.0) | 193 (64.3) |
| >=10 minutes, (%) | 14 (14.1) | 16 (32.7) | 25 (46.3) | 53 (50.5) | 60 (65.2) | 154 (51.3) |
| >=15 minutes, (%) | 8 (8.1) | 10 (20.4) | 15 (27.8) | 39 (37.1) | 40 (43.5) | 104 (34.7) |
| >=20 minutes, (%) | 3 (3.0) | 5 (10.2) | 7 (13.0) | 26 (24.8) | 26 (28.3) | 64 (21.3) |
| >=25 minutes, (%) | 2 (2.0) | 0 | 3 (5.6) | 13 (12.4) | 12 (13.0) | 28 (9.3) |
| >=30 mintues, (%) | 2 (2.0) | 0 | 1 (1.9) | 0 | 6 (6.5) | 7 (2.3) |

N = number of subjects within each treatment group.
Percentages are based on n-the number of subjects with non-missing value at baseline and at the specific visit.
MWT = Maintenance of Wakefulness Test
MWT sleep latency ranges from 0 to 40 minutes, with higher scores indicating greater ability to stay awake; a positive change from baseline represents improvement in the sleep latency time. Mean sleep latency defined as the average of the first four MWT trial's measurements, if three or four of them are non-missing.

TABLE 3

TEAEs Occurring in the Titration and Stable-Dose Phases in the Safety Population

| | Incidence, n (%) | |
|---|---|---|
| TEAE | Titration Phase, All JZP-110 Doses (n = 174) | Stable-Dose Phase, All JZP-110 Doses (n = 157) |
| Any TEAE | 85 (48.9) | 16 (10.2) |
| Serious TEAE | 0 | 0 |
| TEAE leading to withdrawal | 6 (3.4) | 0 |
| Most common TEAEs[a] | | |
| Headache | 17 (9.8) | 2 (1.3) |
| Dry mouth | 12 (6.9) | 1 (0.6) |
| Nausea | 12 (6.9) | 1 (0.6) |
| Dizziness | 10 (5.7) | 3 (1.9) |
| Insomnia | 10 (5.7) | 1 (0.6) |
| Palpitations | 8 (4.6) | 1 (0.6) |
| Anxiety | 7 (4.0) | 1 (0.6) |
| Dyspepsia | 4 (2.3) | 0 |
| Diarrhea | 4 (2.3) | 0 |

[a]Occurring in ≥5% of patients in any treatment group.
TEAEs, treatment-emergent adverse events.

TABLE 4

TEAEs Occurring During the Randomized Withdrawal Phase

| | Incidence, n (%) | |
|---|---|---|
| TEAE | Placebo (n = 62) | All JZP-110 Doses (n = 62) |
| Any TEAE | 6 (9.7) | 18 (29.0) |
| Serious TEAEs | 0 | 0 |
| TEAEs leading to withdrawal | 0 | 0 |
| Most common TEAEs[a] | | |
| Nasopharyngitis | 0 | 3 (4.8) |
| Aphthous stomatitis | 0 | 1 (1.6) |
| Upper respiratory tract infection | 0 | 1 (1.6) |
| Cough | 0 | 1 (1.6) |

[a]Occurring in ≥5% of patients in any treatment group.
TEAEs, treatment-emergent adverse events.

TABLE 5

Baseline Demographic and Clinical Characteristics of the Safety Population

| | | JZP-110 | | | |
|---|---|---|---|---|---|
| Variable | Placebo (n = 119) | 37.5 mg (n = 58) | 75 mg (n = 62) | 150 mg (n = 117) | 300 mg (n = 118) |
| Baseline Demographics | | | | | |
| Age, years, mean (SD) | 54.1 (11.4) | 57.1 (10.2) | 54.4 (11.5) | 52.7 (10.6) | 53.2 (10.6) |
| Sex, n (%) | | | | | |
| Male | 77 (64.7) | 39 (67.2) | 35 (56.5) | 72 (61.5) | 74 (62.7) |
| Female | 42 (35.3) | 19 (32.8) | 27 (43.5) | 45 (38.5) | 44 (37.3) |
| Race, n (%) | | | | | |
| Asian | 4 (3.4) | 3 (5.2) | 1 (1.6) | 3 (2.6) | 6 (5.1) |
| Black or African American | 26 (21.8) | 10 (17.2) | 14 (22.6) | 18 (15.4) | 21 (17.8) |
| White | 87 (73.1) | 45 (77.6) | 46 (74.2) | 93 (79.5) | 90 (76.3) |
| Other | 2 (1.7) | 0 | 1 (1.6) | 3 (2.6) | 1 (0.8) |
| BMI, kg/m$^2$, mean (SD) | 33.1 (5.2) | 34.1 (5.3) | 33.4 (5.7) | 33.3 (4.8) | 32.9 (5.6) |
| Primary OSA therapy, n (%) | | | | | |
| Adherence | 83 (69.7) | 40 (69.0) | 45 (72.6) | 80 (68.4) | 86 (72.9) |
| Non-adherence | 36 (30.3) | 18 (31.0) | 17 (27.4) | 37 (31.6) | 32 (27.1) |
| Baseline Clinical Characteristics | | | | | |
| MWT sleep latency, minutes, mean (SD) | 12.4 (7.2) | 13.6 (8.1) | 13.1 (7.2) | 12.5 (7.2) | 12.0 (7.3) |
| ESS score, mean (SD) | 15.6 (3.3) | 15.1 (3.5) | 14.8 (3.5) | 15.1 (3.4) | 15.2 (3.1) |
| Baseline CGI-S, n (%) | | | | | |
| 1 = Normal, not at all ill | 0 | 0 | 0 | 0 | 0 |
| 2 = Borderline ill | 3 (2.5) | 1 (1.7) | 1 (1.6) | 2 (1.7) | 1 (0.8) |
| 3 = Mildly ill | 8 (6.7) | 5 (8.6) | 4 (6.5) | 7 (6.0) | 10 (8.5) |
| 4 = Moderately ill | 48 (40.3) | 28 (48.3) | 31 (50.0) | 53 (45.3) | 44 (37.3) |
| 5 = Markedly ill | 39 (32.8) | 14 (24.1) | 15 (24.2) | 41 (35.0) | 44 (37.3) |
| 6 = Severely ill | 15 (12.6) | 9 (15.5) | 7 (11.3) | 14 (12.0) | 17 (14.4) |
| 7 = Among the most extremely ill | 4 (3.4) | 1 (1.7) | 3 (4.8) | 0 | 2 (1.7) |
| Missing | 2 (1.7) | 0 | 1 (1.6) | 0 | 0 |
| FOSQ-10, mean (SD)[a] | 13.5 (3.1) | 14.0 (3.4) | 13.6 (3.0) | 14.1 (2.7) | 14.2 (3.0) |
| Percent impairment while working, mean (SD)[a] | 37.4 (26.0) | 34.7 (23.6) | 37.4 (26.2) | 33.7 (24.6) | 33.7 (26.7) |

[a]mITT population: placebo, n = 114; JZP-110 37.5 mg, n = 56; 75 mg, n = 58; 150 mg, n = 116; 300 mg, n = 115.
BMI, body mass index; CGI-S, Clinical Global Impression of Severity[5]; CPAP, continuous positive airway pressure; ESS, Epworth Sleepiness Scale; FOSQ-10, Functional Outcomes of Sleep questionnaire short version; MWT, Maintenance of Wakefulness Test; OSA, obstructive sleep apnea; SD, standard deviation.

TABLE 6

Observed Values at Week 12 (mITT Population)

| Endpoint | Placebo (n = 114) | JZP-110 37.5 mg (n = 56) | JZP-110 75 mg (n = 58) | JZP-110 150 mg (n = 116) | JZP-110 300 mg (n = 115) |
|---|---|---|---|---|---|
| MWT sleep latency, min, mean (SD)[a] | 13.4 (10.3) | 18.6 (12.3)* | 21.8 (11.3)† | 23.6 (11.0)† | 25.3 (11.3)† |
| ESS score, mean (SD) | 12.2 (4.5) | 9.7 (5.3)* | 10.0 (5.2)* | 7.5 (4.7)† | 7.1 (4.8)† |
| PGI-C, %[b] | 49.1 | 55.4 | 72.4* | 89.7† | 88.7† |

*$P < 0.05$ and
†$P < 0.0001$ relative to placebo.

[a]On the first 4 trials of a 5-trial MWT.

[b]Percentage of patients who reported "minimally improved," "much improved," or "very much improved."

ESS, Epworth Sleepiness Scale; mITT, modified intent-to-treat; MWT, Maintenance of Wakefulness Test; PGI-C, Patient Global Impression of Change; SD, standard deviation.

TABLE 7

Incidence of TEAEs in the Safety Population

| | | incidence, n (%) | | | | |
| --- | --- | --- | --- | --- | --- | --- |
| | | JZP-110 | | | | |
| TEAE | Placebo (n = 119) | 37.5 mg (n = 58) | 75 mg (n = 62) | 150 mg (n = 117) | 300 mg (n=118) | All doses (n = 355) |
| Any TEAE | 57 (47.9) | 37 (63.8) | 30 (48.4) | 83 (70.9) | 91 (77.1) | 241 (67.9) |
| Serious TEAEs | 2 (1.7) | 2 (3.4) | 0 | 1 (0.9) | 0 | 3 (0.8) |
| Discontinuations due to TEAEs | 4 (3.4) | 3 (5.2) | 2 (3.2) | 5 (4.3) | 15 (12.7) | 25 (7.0) |
| Most common TEAEs[a] | | | | | | |
| Headache | 10 (8.4) | 4 (6.9) | 5 (8.1) | 10 (8.5) | 17 (14.4) | 36 (10.1) |
| Nausea | 7 (5.9) | 3 (5.2) | 3 (4.8) | 10 (8.5) | 12 (10.2) | 28 (7.9) |
| Decreased appetite | 1 (0.8) | 1 (1.7) | 3 (4.8) | 9 (7.7) | 14 (11.9) | 27 (7.6) |
| Anxiety | 0 | 1 (1.7) | 2 (3.2) | 6 (5.1) | 16 (13.6) | 25 (7.0) |
| Nasopharyngitis | 8 (6.7) | 2 (3.4) | 1 (1.6) | 7 (6.0) | 8 (6.8) | 18 (5.1) |
| Diarrhea | 1 (0.8) | 1 (1.7) | 3 (4.6) | 5 (4.3) | 8 (6.6) | 17 (4.8) |
| Dry mouth | 2 (1.7) | 1 (1.7) | 1 (1.6) | 5 (4.3) | 9 (7.6) | 16 (4.5) |
| Insomnia | 2 (1.7) | 1 (1.7) | 0 | 3 (2.6) | 11 (9.3) | 15 (4.2) |
| Feeling jittery | 0 | 3 (5.2) | 3 (4.8) | 1 (0.9) | 7 (5.9) | 14 (3.9) |
| Sinusitis | 3 (2.5) | 1 (1.7) | 4 (6.5) | 0 | 3 (2.5) | 8 (2.3) |
| Irritability | 0 | 3 (5.2) | 0 | 4 (3.4) | 1 (0.8) | 8 (2.3) |
| Pruritus | 0 | 3 (5.2) | 0 | 1 (0.9) | 0 | 4 (1.1) |

[a]≥5% in any treatment group.
TEAEs, treatment-emergent adverse events.

TABLE 8

Baseline Demographic and Clinical Characteristics of the Safety Population

| | | JZP-110 | | | |
| --- | --- | --- | --- | --- | --- |
| Variable | Placebo (n = 119) | 37.5 mg (n = 58) | 75 mg (n = 62) | 150 mg (n = 117) | 300 mg (n = 118) |
| Baseline Demographics | | | | | |
| Age, years, mean (SD) | 54.1 (11.4) | 57.1 (10.2) | 54.4 (11.5) | 52.7 (10.6) | 53.2 (10.6) |
| Sex, n (%) | | | | | |
| Male | 77 (64.7) | 39 (67.2) | 35 (56.5) | 72 (61.5) | 74 (62.7) |
| Female | 42 (35.3) | 19 (32.8) | 27 (43.5) | 45 (38.5) | 44 (37.3) |
| Race, n (%) | | | | | |
| Asian | 4 (3.4) | 3 (5.2) | 1 (1.6) | 3 (2.6) | 6 (5.1) |
| Black or African-American | 26 (21.8) | 10 (17.2) | 14 (22.6) | 18 (15.4) | 21 (17.8) |
| White | 87 (73.1) | 45 (77.6) | 46 (74.2) | 93 (79.5) | 90 (76.3) |
| Other | 2 (1.6) | 0 | 1 (1.6) | 3 (2.6) | 1 (0.8) |
| Body mass index, kg/m$^2$, mean (SD) | 33.1 (5.2) | 34.1 (5.3) | 33.41 (5.7) | 33.3 (4.8) | 32.9 (5.6) |
| Baseline Clinical Characteristics | | | | | |
| MWT sleep latency, minutes, mean (SD) | 12.4 (7.2) | 13.6 (8.1) | 13.1 (7.2) | 12.5 (7.2) | 12.0 (7.3) |
| ESS score, mean (SD) | 15.6 (3.3) | 15.1 (3.5) | 14.8 (3.5) | 15.1 (3.4) | 15.2 (3.1) |
| Baseline CGI-S, n (%) | | | | | |
| 1 = Normal, not at all ill | 0 | 0 | 0 | 0 | 0 |
| 2 = Borderline ill | 3 (2.5) | 1 (1.7) | 1 (1.6) | 2 (1.7) | 1 (0.8) |
| 3 = Mildly ill | 8 (6.7) | 5 (8.6) | 4 (6.5) | 7 (6.0) | 10 (8.5) |
| 4 = Moderately ill | 48 (40.3) | 28 (48.3) | 31 (50.0) | 53 (45.3) | 44 (37.3) |

TABLE 8-continued

Baseline Demographic and Clinical Characteristics of the Safety Population

| | | JZP-110 | | | |
|---|---|---|---|---|---|
| Variable | Placebo (n = 119) | 37.5 mg (n = 58) | 75 mg (n = 62) | 150 mg (n = 117) | 300 mg (n = 118) |
| 5 = Markedly ill | 39 (32.8) | 14 (24.1) | 15 (24.2) | 41 (35.0) | 44 (37.3) |
| 6 = Severely ill | 15 (12.6) | 9 (15.5) | 7 (11.3) | 14 (12.0) | 17 (14.4) |
| 7 = Among the most extremely ill | 4 (3.4) | 1 (1.7) | 3 (4.8) | 0 | 2 (1.7) |
| Missing | 2 (1.7) | 0 | 1 (1.6) | 0 | 0 |
| SF-36v2, mean (SD)[a] | | | | | |
| Physical Function | 48.2 (8.5) | 46.1 (8.6) | 49.4 (7.8) | 48.2 (8.3) | 48.0 (8.2) |
| Role Physical | 44.9 (9.7) | 43.2 (9.8) | 45.4 (10.1) | 45.2 (9.2) | 43.0 (9.8) |
| Bodily Pain | 48.5 (8.0) | 46.5 (10.3) | 47.4 (8.8) | 48.7 (9.6) | 48.3 (9.7) |
| General Health | 49.9 (9.6) | 49.8 (8.4) | 49.4 (9.2) | 48.5 (9.1) | 49.5 (8.8) |
| Vitality | 45.2 (8.6) | 44.9 (10.4) | 45.3 (9.7) | 45.3 (8.1) | 44.3 (9.8) |
| Social Functioning | 48.2 (9.4) | 47.4 (9.0) | 48.4 (9.2) | 49.0 (8.8) | 47.5 (10.1) |
| Role Emotional | 50.7 (8.9) | 46.9 (11.6) | 48.4 (10.2) | 49.1 (9.4) | 50.1 (9.0) |
| Mental Health | 51.8 (7.9) | 53.1 (7.6) | 52.2 (7.5) | 51.9 (6.9) | 51.9 (7.7) |
| Physical Component Summary | 46.3 (7.8) | 44.5 (8.4) | 46.9 (8.8) | 46.3 (8.5) | 45.9 (8.9) |
| Mental Component Summary | 50.7 (9.1) | 50.3 (9.4) | 49.8 (8.7) | 50.3 (8.0) | 50.3 (8.5) |
| EQ-5D-5L, mean (SD)[a] | | | | | |
| VAS | 76.8 (15.8) | 77.0 (16.4) | 77.9 (13.1) | 76.8 (14.8) | 76.8 (14.9) |
| Index score | 0.85 (0.11) | 0.83 (0.13) | 0.84 (0.11) | 0.84 (0.11) | 0.84 (0.10) |

[a]mITT population: Placebo, n = 114; JZP-110 37.5 mg, n = 56; 75 mg, n = 58; 150 mg, n = 116; 300 mg, n = 115.
CGI-S, Clinical Global Impression of Severity[9]; EQ-5D-5L, 5-dimension, 5-level EuroQoL; mITT, modified intent-to-treat; SF-36v2, 36-item Short Form Health Survey version 2; SD, standard deviation; VAS, visual analog scale.

TABLE 9

Observed Values at Week 12 (mITT Population)

| Endpoint | Placebo (n = 114) | JZP-110 37.5 mg (n = 56) | JZP-110 75 mg (n = 58) | JZP-110 150 mg (n = 116) | JZP-110 300 mg (n = 115) |
|---|---|---|---|---|---|
| MWT sleep latency, min, mean (SD)[a] | 13.4 (10.3) | 18.6 (12.3)* | 21.8 (11.3)† | 23.6 (11.0)† | 25.3 (11.3)† |
| ESS score, mean (SD) | 12.2 (4.5) | 9.7 (5.3)* | 10.0 (5.2)* | 7.5 (4.7)† | 7.1 (4.8)† |
| PGI-C, %[b] | 49.1 | 55.4 | 72.4* | 89.7† | 88.7† |

*$P < 0.05$ and

†$P < 0.0001$ relative to placebo.

[a]On the first 4 trials of a 5-trial MWT.

[b]Percentage of patients who reported "minimally improved," "much improved," or "very much improved."

ESS, Epworth Sleepiness Scale; mITT, modified intent-to-treat; MWT, Maintenance of Wakefulness Test; PGI-C, Patient Global Impression of Change; SD, standard deviation.

TABLE 10

Incidence of TEAEs in the Safety Population

| | | | incidence, n (%) | | | |
|---|---|---|---|---|---|---|
| | | | JZP-110 | | | |
| TEAE | Placebo (n = 119) | 37.5 mg (n = 58) | 75 mg (n = 62) | 150 mg (n = 117) | 300 mg (n=118) | All doses (n = 355) |
| Any TEAE | 57 (47.9) | 37 (63.8) | 30 (48.4) | 83 (70.9) | 91 (77.1) | 241 (67.9) |
| Serious TEAEs | 2 (1.7) | 2 (3.4) | 0 | 1 (0.9) | 0 | 3 (0.8) |
| Discontinuations due to TEAEs | 4 (3.4) | 3 (5.2) | 2 (3.2) | 5 (4.3) | 15 (12.7) | 25 (7.0) |
| Most common TEAEs[a] | | | | | | |
| Headache | 10 (8.4) | 4 (6.9) | 5 (8.1) | 10 (8.5) | 17 (14.4) | 36 (10.1) |
| Nausea | 7 (5.9) | 3 (5.2) | 3 (4.8) | 10 (8.5) | 12 (10.2) | 28 (7.9) |
| Decreased appetite | 1 (0.8) | 1 (1.7) | 3 (4.8) | 9 (7.7) | 14 (11.9) | 27 (7.6) |
| Anxiety | 0 | 1 (1.7) | 2 (3.2) | 6 (5.1) | 16 (13.6) | 25 (7.0) |
| Nasopharyngitis | 8 (6.7) | 2 (3.4) | 1 (1.6) | 7 (6.0) | 8 (6.8) | 18 (5.1) |
| Diarrhea | 1 (0.8) | 1 (1.7) | 3 (4.8) | 5 (4.3) | 8 (6.6) | 17 (4.8) |
| Dry mouth | 2 (1.7) | 1 (1.7) | 1 (1.6) | 5 (4.3) | 9 (7.6) | 16 (4.5) |
| Insomnia | 2 (1.7) | 1 (1.7) | 0 | 3 (2.6) | 11 (9.3) | 15 (4.2) |
| Feeling jittery | 0 | 3 (5.2) | 3 (4.8) | 1 (0.9) | 7 (5.9) | 14 (3.9) |
| Sinusitis | 3 (2.5) | 1 (1.7) | 4 (6.5) | 0 | 3 (2.5) | 8 (2.3) |
| Irritability | 0 | 3 (5.2) | 0 | 4 (3.4) | 1 (0.8) | 8 (2.3) |
| Pruritus | 0 | 3 (5.2) | 0 | 1 (0.9) | 0 | 4 (1.1) |

[a] ≥5% in any treatment group.
TEAEs, treatment-emergent adverse events.

TABLE 11

Baseline Demographic and Clinical Characteristics of the mITT Population

| | | JZP-110 | | |
|---|---|---|---|---|
| Variable | Placebo (n = 58) | 75 mg (n = 59) | 150 mg (n = 55) | 300 mg (n = 59) |
| Demographics | | | | |
| Age, years, mean (SD) | 36.2 (15.2) | 36.5 (12.8) | 38.0 (13.0) | 34.3 (11.5) |
| Sex, n (%) | | | | |
| Male | 24 (41.4) | 22 (37.3) | 16 (29.1) | 19 (32.2) |
| Female | 34 (58.6) | 37 (62.7) | 39 (70.9) | 40 (67.8) |
| Race, n (%) | | | | |
| Asian | 0 | 0 | 3 (5.5) | 3 (5.1) |
| Black or African- American | 10 (17.2) | 12 (20.3) | 6 (10.9) | 5 (8.5) |
| White | 46 (79.3) | 46 (78.0) | 44 (80.0) | 48 (81.4) |
| Other | 2 (3.4) | 1 (1.7) | 2 (3.6) | 3 (5.1) |
| BMI, kg/m$^2$, mean (SD) | 29.3 (5.8) | 27.9 (5.4) | 27.8 (5.8) | 28.1 (6.3) |
| Presence of cataplexy, n (%) | 29 (50.0) | 31 (52.5) | 27 (49.1) | 30 (50.8) |
| Clinical characteristics | | | | |
| MWT sleep latency, minutes, mean (SD) | 6.2 (5.7) | 7.5 (5.4) | 7.9 (5.7) | 8.7 (6.2) |
| ESS score, mean (SD) | 17.3 (2.9) | 17.3 (3.5) | 17.0 (3.6) | 17.2 (2.8) |
| Baseline CGI-S, n (%) | | | | |
| 1 = Normal, not at all ill | 0 | 0 | 0 | 0 |
| 2 = Borderline ill | 0 | 0 | 0 | 0 |
| 3 = Mildly ill | 1 (1.7) | 3 (5.1) | 3 (5.5) | 1 (1.7) |
| 4 = Moderately ill | 14 (24.1) | 14 (23.7) | 15 (27.3) | 17 (28.8) |
| 5 = Markedly ill | 25 (43.1) | 20 (33.9) | 23 (41.8) | 21 (35.6) |
| 6 = Severely ill | 13 (22.4) | 17 (28.8) | 12 (21.8) | 12 (20.3) |
| 7 = Among the most extremely ill | 4 (6.9) | 5 (8.5) | 2 (3.6) | 8 (13.6) |
| Missing | 1 (1.7) | 0 | 0 | 0 |

BMI, body mass index; CGI-S, Clinical Global Impression of Severity; ESS, Epworth Sleepiness Scale; mITT, modified intent-to-treat; MWT, Maintenance of Wakefulness Test; SD, standard deviation.

TABLE 12

Hierarchical Testing of Co-Primary and Key Secondary Efficacy Endpoints in the mITT Population

| Endpoint | JZP-110 300 mg | JZP-110 150 mg | JZP-110 75 mg |
|---|---|---|---|
| MWT | <0.0001 | <0.0001 | .1595 |
| ESS | <0.0001 | <0.0001 | 0.0211 |
| PGI-C | <0.0001 | <0.0001 | 0.0023* |

*Nominal P-value since below the hierarchical break

TABLE 13

MWT Mean Sleep Latency (minutes): Summary of Change from Baseline Categories by Visit (mITT Population)

| Parameter Visit | Placebo N = 58 | 75 mg N = 59 | 150 mg N = 55 | 300 mg N = 59 | Combined JZP-110 N = 173 |
|---|---|---|---|---|---|
| Increase from Baseline Week 1 | | | | | |
| n | 23 | 29 | 22 | 25 | 76 |
| >=5 minutes, (%) | 5 (21.7) | 10 (34.5) | 15 (68.2) | 16 (64.0) | 41 (53.9) |
| >=10 minutes, (%) | 4 (17.4) | 7 (24.1) | 11 (50.0) | 14 (56.0) | 32 (42.1) |
| >=15 minutes, (%) | 2 (8.7) | 5 (17.2) | 5 (22.7) | 11 (44.0) | 21 (27.6) |
| >=20 minutes, (%) | 1 (4.3) | 3 (10.3) | 2 (9.1) | 8 (32.0) | 13 (17.1) |
| >=25 minutes, (%) | 1 (4.3) | 1 (3.4) | 0 | 6 (24.0) | 7 (9.2) |
| >=30 minutes, (%) | 0 | 0 | 0 | 5 (20.0) | 5 (6.6) |
| Week 4 | | | | | |
| n | 52 | 50 | 49 | 52 | 151 |
| >=5 minutes, (%) | 12 (23.1) | 21 (42.0) | 30 (61.2) | 36 (69.2) | 87 (57.6) |
| >=10 minutes, (%) | 5 (9.6) | 12 (24.0) | 21 (42.9) | 28 (53.8) | 61 (40.4) |
| >=15 minutes, (%) | 1 (1.9) | 6 (12.0) | 15 (30.6) | 19 (36.5) | 40 (26.5) |
| >=20 minutes, (%) | 1 (1.9) | 3 (6.0) | 8 (16.3) | 13 (25.0) | 24 (15.9) |
| >=25 minutes, (%) | 0 | 0 | 5 (10.2) | 9 (17.3) | 14 (9.3) |
| >=30 minutes, (%) | 0 | 0 | 0 | 7 (13.5) | 7 (4.6) |
| Week 12 | | | | | |
| n | 51 | 46 | 50 | 40 | 136 |
| >=5 minutes, (%) | 11 (21.6) | 19 (41.3) | 29 (58.0) | 24 (60.0) | 72 (52.9) |
| >=10 minutes, (%) | 6 (11.8) | 9 (19.6) | 24 (48.0) | 20 (50.0) | 53 (39.0) |
| >=15 minutes, (%) | 2 (3.9) | 7 (15.2) | 18 (36.0) | 15 (37.5) | 40 (29.4) |
| >=20 minutes, (%) | 2 (3.9) | 4 (8.7) | 9 (18.0) | 11 (27.5) | 24 (17.6) |
| >=25 minutes, (%) | 1 (2.0) | 1 (2.2) | 4 (8.0) | 6 (15.0) | 11 (8.1) |
| >=30 minutes, (%) | 0 | 0 | 1 (2.0) | 3 (7.5) | 4 (2.9) |

N = number of subjects within each treatment group. Percentages are based on n—the number of subjects with non-missing value at baseline and at the specific visit.
MWT = Maintenance of Wakefulness Test
MWT sleep latency ranges from 0 to 40 minutes, with higher scores indicating greater ability to stay awake; a positive change from baseline represents improvement in the sleep latency time. Mean sleep latency defined as the average of the first four MWT trial's measurements, if three or four of them are non-missing.

TABLE 14

TEAEs in the Safety Population

| | Incidence, n (%) | | | | |
|---|---|---|---|---|---|
| | | JZP-110 | | | |
| | Placebo (n = 59) | All JZP-110 (n = 177) | 75 mg (n = 59) | 150 mg (n = 59) | 300 mg (n = 59) |
| Event | | | | | |
| Any TEAE | 27 (45.8) | 121 (68.4) | 34 (57.6) | 47 (79.7) | 40 (67.8) |
| Serious TEAEs | 0 | 1 (0.6) | 0 | 1 (1.7) | 0 |
| Discontinuations due to TEAEs | 1 (1.7) | 9 (5.1) | 1 (1.7) | 3 (5.1) | 5 (8.5) |
| Most common TEAEs* | | | | | |
| Headache | 3 (5.1) | 38 (21.5) | 6 (10.2) | 14 (23.7) | 18 (30.5) |
| Nausea | 1 (1.7) | 19 (10.7) | 3 (5.1) | 6 (10.2) | 10 (16.9) |
| Decreased appetite | 1 (1.7) | 19 (10.7) | 5 (8.5) | 5 (8.5) | 9 (15.3) |

TABLE 14-continued

TEAEs in the Safety Population

| | | Incidence, n (%) | | | |
| | | | JZP-110 | | |
| | Placebo (n = 59) | All JZP-110 (n = 177) | 75 mg (n = 59) | 150 mg (n = 59) | 300 mg (n = 59) |
|---|---|---|---|---|---|
| Nasopharyngitis | 3 (5.1) | 16 (9.0) | 5 (8.5) | 8 (13.6) | 3 (5.1) |
| Dry mouth | 2 (3.4) | 13 (7.3) | 3 (5.1) | 4 (6.8) | 6 (10.2) |
| Anxiety | 1 (1.7) | 9 (5.1) | 1 (1.7) | 3 (5.1) | 5 (8.5) |
| Diarrhea | 1 (1.7) | 8 (4.5) | 2 (3.4) | 3 (5.1) | 3 (5.1) |
| Dyspepsia | 0 | 6 (3.4) | 1 (1.7) | 2 (3.4) | 3 (5.1) |
| Dizziness | 2 (3.4) | 6 (3.4) | 2 (3.4) | 1 (1.7) | 3 (5.1) |
| Fatigue | 0 | 5 (2.8) | 0 | 2 (3.4) | 3 (5.1) |
| Weight decreased | 0 | 5 (2.8) | 1 (1.7) | 1 (1.7) | 3 (5.1) |
| Upper respiratory tract infection | 1 (1.7) | 5 (2.8) | 1 (1.7) | 4 (6.8) | 0 |
| Insomnia | 0 | 5 (2.8) | 2 (3.4) | 0 | 3 (5.1) |
| Constipation | 1 (1.7) | 4 (2.3) | 3 (5.1) | 1 (1.7) | 0 |
| Influenza | 3 (5.1) | 4 (2.3) | 2 (3.4) | 1 (1.7) | 1 (1.7) |
| Heart rate increased | 0 | 4 (2.3) | 0 | 0 | 4 (6.8) |
| Weight Increased | 3 (5.1) | 3 (1.7) | 2 (3.4) | 0 | 1 (1.7) |

*≥5% in any treatment group. TEAEs, treatment-emergent adverse events.

What is claimed is:

1. A method of treating excessive sleepiness in a human patient with obstructive sleep apnea (OSA) in need thereof, said method comprising orally administering [R]-2-amino-3-phenylpropylcarbamate (APC) or a pharmaceutically acceptable salt thereof to the human patient in accordance with a dosing regimen comprising a once-daily dose of 75 mg for at least 3 days followed by a once-daily dose of 150 mg, wherein the once-daily dose of 150 mg is the maximum dose in the dosing regimen, and wherein the APC or pharmaceutically acceptable salt thereof effects a reduction in excessive sleepiness as measured by Epworth Sleepiness Scale (ESS) score to below 10 points at the 12th week of the dosing regimen.

2. The method of claim 1, wherein the dosing regimen comprises a once-daily dose of 75 mg for 3 days followed by a once-daily dose of 150 mg.

3. The method of claim 1, wherein the patient with OSA has a baseline ESS score greater than 10.

4. The method of claim 1, wherein the APC or pharmaceutically acceptable salt thereof effects a reduction in excessive sleepiness as measured by ESS score by at least 5 points at the 12th week of the dosing regimen.

5. The method of claim 1, wherein the excessive sleepiness is excessive daytime sleepiness.

6. The method of claim 1, wherein the APC is provided as a pharmaceutically acceptable salt of APC.

7. The method of claim 1, wherein the APC is provided in the form of APC hydrochloride salt.

8. The method of claim 1, wherein the daily dose is administered at least 10 hours before the patient's bedtime.

9. The method of claim 1, wherein the daily dose is administered within 1 hour of the patient waking.

10. The method of claim 1, wherein the patient is an adult.

* * * * *

UNITED STATES PATENT AND TRADEMARK OFFICE
CERTIFICATE OF CORRECTION

PATENT NO.       : 10,912,754 B2
APPLICATION NO.  : 16/877717
DATED            : February 9, 2021
INVENTOR(S)      : Carter et al.

Page 1 of 1

It is certified that error appears in the above-identified patent and that said Letters Patent is hereby corrected as shown below:

In the Specification

Column 4, Line 34: Please correct "950%" to read -- 95% --

Signed and Sealed this
Eighth Day of June, 2021

Drew Hirshfeld
*Performing the Functions and Duties of the*
*Under Secretary of Commerce for Intellectual Property and*
*Director of the United States Patent and Trademark Office*